(12) United States Patent
Stecco et al.

(10) Patent No.: US 12,004,777 B2
(45) Date of Patent: *Jun. 11, 2024

(54) STRENGTH AND FATIGUE LIFE IMPROVEMENTS FOR ACTIVE BONE AND JOINT STABILIZATION DEVICES

(71) Applicant: MEDEON BIODESIGN, INC., Taipei (TW)

(72) Inventors: Kathryn A. Stecco, San Jose, CA (US); Frank P. Becking, La Canada-Flintridge, CA (US); Carlos Castro, San Jose, CA (US); Roger William Sharpe, Mountain View, CA (US); Damon Covell Campbell, Pacific Grove, CA (US)

(73) Assignee: MEDEON BIODESIGN, INC., Taipei (TW)

( * ) Notice: Subject to any disclaimer, the term of this patent is extended or adjusted under 35 U.S.C. 154(b) by 148 days.

This patent is subject to a terminal disclaimer.

(21) Appl. No.: 17/331,192

(22) Filed: May 26, 2021

(65) Prior Publication Data

US 2021/0353332 A1 Nov. 18, 2021

Related U.S. Application Data

(63) Continuation of application No. 16/855,584, filed on Apr. 22, 2020, now Pat. No. 11,045,225.

(60) Provisional application No. 63/001,107, filed on Mar. 27, 2020, provisional application No. 62/914,172, filed on Oct. 11, 2019, provisional application No. 62/896,302, filed on Sep. 5, 2019, provisional application No. 62/837,579, filed on Apr. 23, 2019.

(51) Int. Cl.
*A61B 17/68* (2006.01)
*A61B 17/84* (2006.01)
*A61B 17/00* (2006.01)
*A61F 2/30* (2006.01)

(52) U.S. Cl.
CPC ............ *A61B 17/683* (2013.01); *A61B 17/68* (2013.01); *A61B 17/842* (2013.01); *A61B 17/844* (2013.01); *A61B 2017/00867* (2013.01); *A61B 2017/681* (2013.01); *A61F 2002/30622* (2013.01)

(58) Field of Classification Search
CPC ............................ A61B 17/683; A61B 17/842
See application file for complete search history.

(56) References Cited

U.S. PATENT DOCUMENTS

| 4,377,872 | A | * | 3/1983 | Daniell, Jr. | ......... | A44C 5/0053 |
| | | | | | | D11/231 |
| 5,549,619 | A | * | 8/1996 | Peters | ................... | A61M 25/02 |
| | | | | | | 606/151 |
| 10,555,766 | B2 | * | 2/2020 | Stecco | ................. | A61B 17/683 |
| 11,045,225 | B2 | * | 6/2021 | Stecco | ................. | A61B 17/842 |

(Continued)

*Primary Examiner* — Christian A Sevilla
(74) *Attorney, Agent, or Firm* — Kurt T. Mulville; VLP Law Group LLP

(57) ABSTRACT

Bone and joint stabilization devices or systems are described that include multiple-layer bodies. The approach offers dramatically improved fatigue life as compared to one-piece spring members that are otherwise similar or comparable. Coordinated improved-strength anchor embodiments, anchor loading tools and methods of use are also described.

15 Claims, 11 Drawing Sheets

(56) References Cited

U.S. PATENT DOCUMENTS

| | | | | |
|---|---|---|---|---|
| 2006/0264944 A1* | 11/2006 | Cole | .................... | A61B 17/725 |
| | | | | 606/62 |
| 2008/0077133 A1* | 3/2008 | Schulze | ............. | A61B 17/8085 |
| | | | | 606/326 |
| 2008/0172097 A1* | 7/2008 | Lerch | .................. | A61B 17/688 |
| | | | | 606/328 |
| 2008/0195119 A1* | 8/2008 | Ferree | .............. | A61B 17/06166 |
| | | | | 606/228 |
| 2014/0228883 A1* | 8/2014 | Blain | .................. | A61B 17/842 |
| | | | | 606/247 |

\* cited by examiner

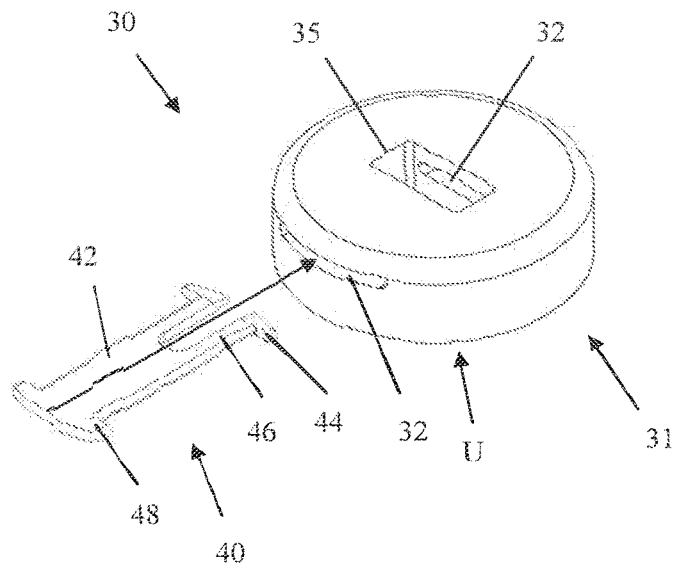
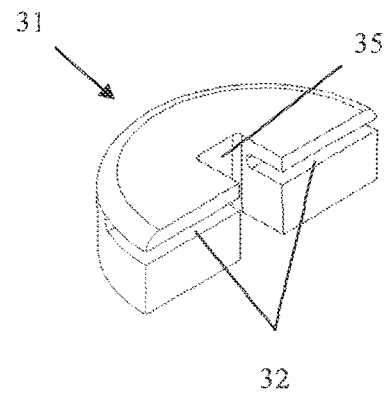
Fig. 3A
Fig. 3B
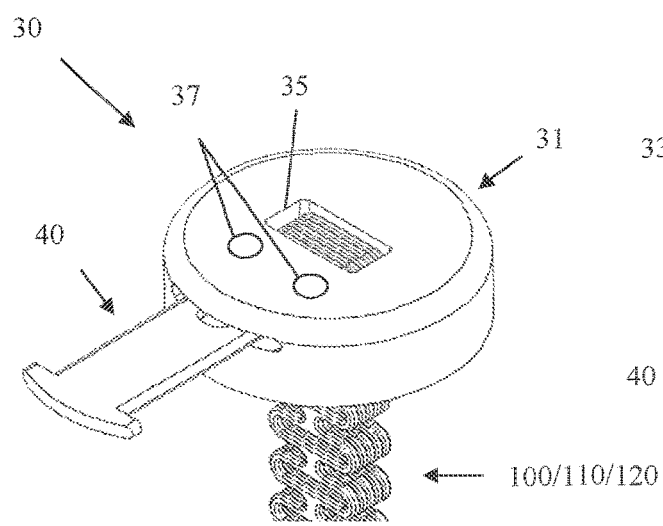
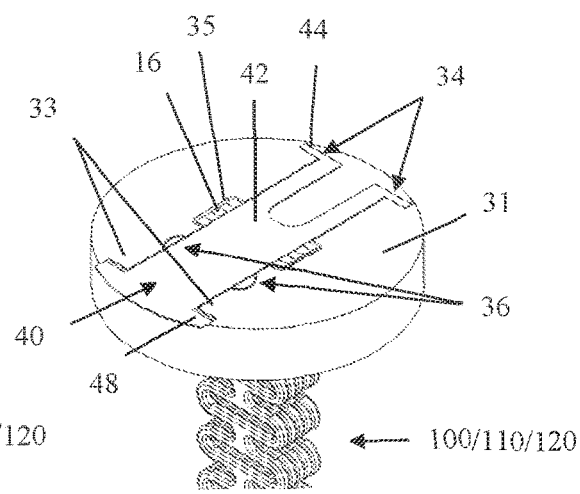
Fig. 4A
Fig. 4B

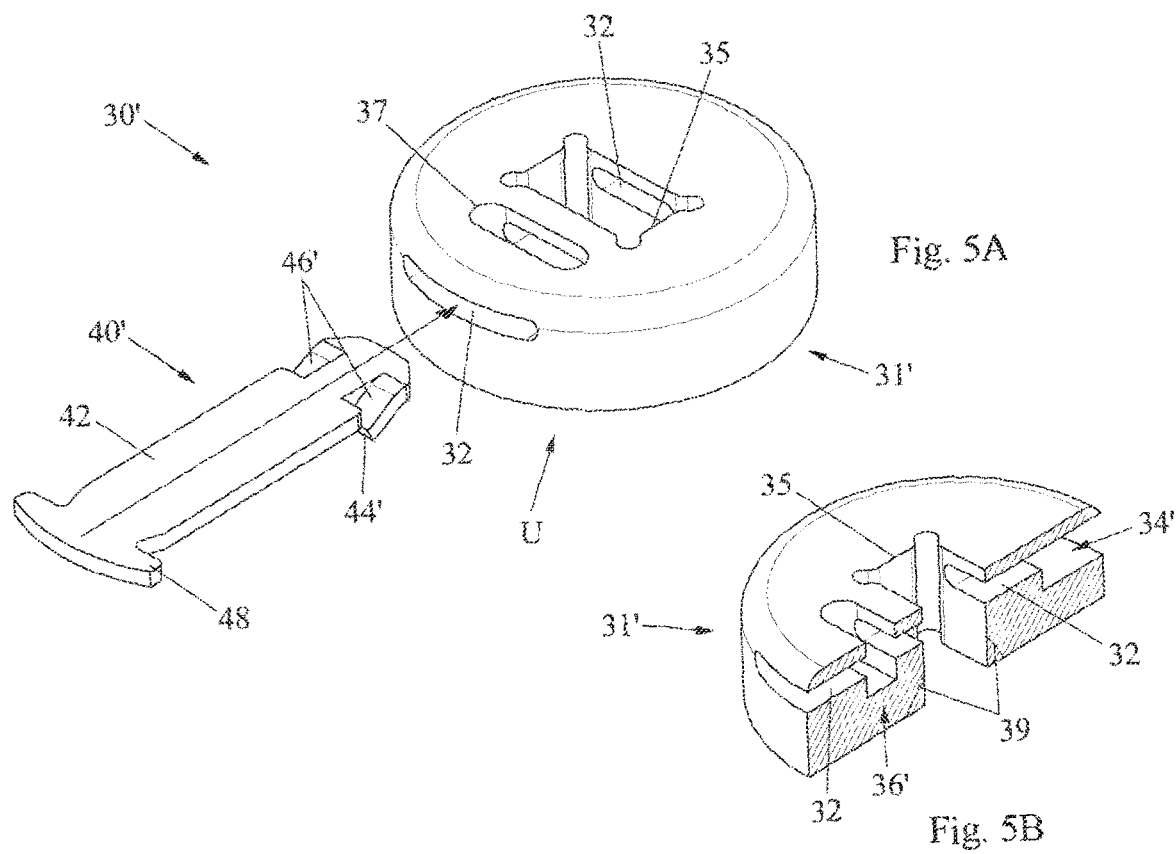
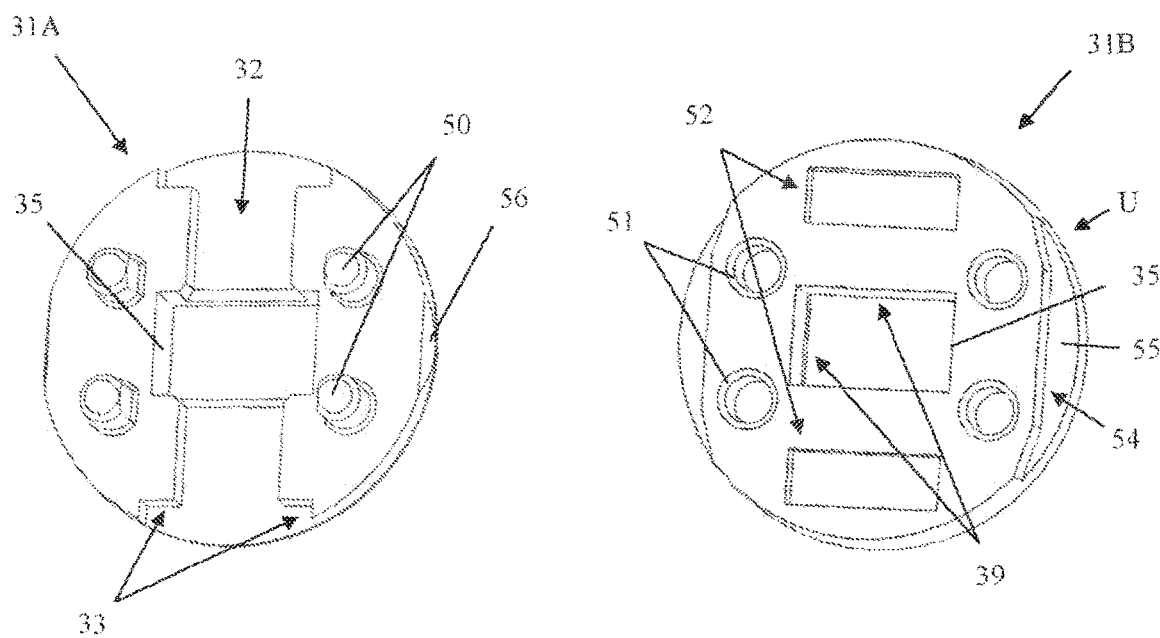
Fig. 6A                    Fig. 6B

STRENGTH AND FATIGUE LIFE IMPROVEMENTS FOR ACTIVE BONE AND JOINT STABILIZATION DEVICES

CROSS-REFERENCE TO RELATED APPLICATIONS

The present application is a continuation of U.S. patent application Ser. 16/855,584, filed Apr. 22, 2020, which claims the benefit of U.S. Provisional Application No. 63/001,107, filed Mar. 27, 2020, U.S. Provisional Application No. 62/914,172, filed Oct. 11, 2019, U.S. Provisional Application No. 62/896,302, filed Sep. 5, 2019, and U.S. Provisional Application No. 62/837,579, filed Apr. 23, 2019, all of which are incorporated herein by reference in their entirety for all purposes.

FIELD

The embodiments described herein are related in the field of surgery and, more particularly, for use in bone fusion, joint stabilization and/or fracture fixation surgery.

BACKGROUND

U.S. Pat. Nos. 10,194,946 and 10,555,766 describe embodiments of bone and/or joint stabilization devices that can be tensioned during a medical procedure to remain active in maintaining compression of associated anatomy during use. In many of these embodiments, an orthopedic surgery device or system includes an elongate member or body including a spring pattern having a plurality of beams, each including a lateral component free to deflect when stretching the elongate body axially. Overall flexibility of the architecture also permits torsional, orthogonal, external and internal rotation, etc. movement of the implant with associated anatomy, enabling full anatomical range of motion.

An anchoring head can receive the elongate body and may secure it with one or more teeth included in a one-way (e.g., ratcheting) interface. Two such anchors may be used or one such anchor may be used with a deployable foot anchor at an opposite end of the elongate body. The referenced "tooth" of the anchoring head may be received part-way into the thickness of the spring member body or it may cross the entire thickness of the spring member. In doing so, the tooth may abut an opposing wall of a feed opening in the anchoring head or overhang further to be supported by an opposing ledge.

Implantable devices covered by the above-referenced patents have been effectively used in human patient treatment. In these surgical procedures, they provided a new and uniquely useful tool in treating traumatic orthopedic injuries. Yet, design improvements leading to higher ultimate strength of certain components and longer cyclic fatigue life are still desirable.

SUMMARY

The subject embodiment or variations are related to those described above, but modified in various ways to achieve significantly longer cyclic fatigue life and/or ultimate strength of certain components. Details of useful spring member architectures, as well as anchoring head, screw and foot features are set forth in U.S. Pat. Nos. 10,194,946 and 10,555,766 as well as WO2016/122944; US2019/0046253; WO2019/032231; U.S. Ser. No. 62/788,343; U.S. Ser. No. 62/788,377; U.S. Ser. No. 62/788,388; and U.S. Ser. No. 16/728,851, all of which are incorporated by reference herein in their entireties for all purposes (especially, as variously referenced below).

More specifically, embodiments hereof include a Nitinol (generally, a NiTi alloy that is superelastic (SE) at human body temperature, i.e., having an $A_f$ below about 37° C.) spring member having a plurality of layers of limited thickness as described below. The approach offers dramatically improved fatigue life as compared to one-piece spring members that are otherwise similar or comparable in overall thickness. The subject multi-layer spring members may be used in a system with anchoring head(s) or a foot as described herein, like those referenced above from the '964 patent (especially those with teeth crossing the entire thickness of the spring member body) or another approach. Still, the coordinated anchoring head embodiments and methods of use (particularly with respect to system tensioning) described herein optionally present certain advantages.

Devices, systems in which the devices (or device components or subcomponents) are included (with or without assembly), methods of use (e.g., with implantation, during treatment of a patient while mending and/or for system removal) and methods of manufacture (including assembly of the various components—as applicable—by a technician prior to sale or during a medical procedure by a surgeon) are all included within the scope of the present disclosure. Such systems may include loading devices or tools as described herein. The subject methods, including methods of use and/or manufacture, may be carried out in any order of the events which is logically possible, as well as any recited order of events. Medical methods may include any of a surgical staff's activities associated with device provision, implant introduction, positioning and/or re-positioning, and surgical access, closure and/or removal (e.g., as in an explant procedure).

BRIEF DESCRIPTION OF THE DRAWINGS

The details of the subject matter set forth herein, both as to its structure and operation, may be apparent by study of the accompanying figures, in which like reference numerals may refer to like parts. The components in the figures are not necessarily to scale, emphasis instead being placed upon illustrating the principles of the subject matter. The illustrations are intended to convey concepts, where relative sizes, shapes and other detailed attributes may either be illustrated schematically rather or precisely. To-scale features (e.g., as from engineering drawings and/or photographs) may be relied upon as antecedent basis for claim support.

FIG. 3A is a perspective view of an example embodiment of an anchoring head (or attachment button) that may be used in the systems of FIGS. 2A-2C and other related embodiments; FIG. 3B is a cross-section view of a body portion of the anchoring head shown in FIG. 3A.

FIG. 4A is a perspective view of the anchoring head of FIG. 3A, together with a multi-layer spring member received therein in preparation for anchoring tooth fixation or deployment; FIG. 4B is a cross-section view of the components in FIG. 4A with the tooth in its fixed or final position to secure the spring member.

FIG. 5A is a perspective view of another example embodiment of an anchoring head that may be used in the systems of FIGS. 2A-2C; FIG. 5B is a cross-section view of a body portion of the anchoring head shown in FIG. 5A.

FIG. 6A is a perspective view of an upper or outer body portion of another anchoring head example embodiment; FIG. 6B is a perspective view of a lower or inner body portion of the same.

DETAILED DESCRIPTION

Various example embodiments are shown in the figures and further described below. Reference is made to these examples in a non-limiting sense, as it should be noted that they are provided to illustrate more broadly applicable aspects of the devices, systems and/or methods. Various changes may be made to these embodiments and equivalents may be substituted without departing from the true spirit and scope of the various embodiments. In addition, many modifications may be made to adapt a particular situation, material, composition of matter, process, process act(s) or step(s) to the objective(s), spirit or scope of the present subject matter. All such modifications are intended to be within the scope of the claims that can be made herein.

Example Embodiments of the Spring Member

Figure 1A:
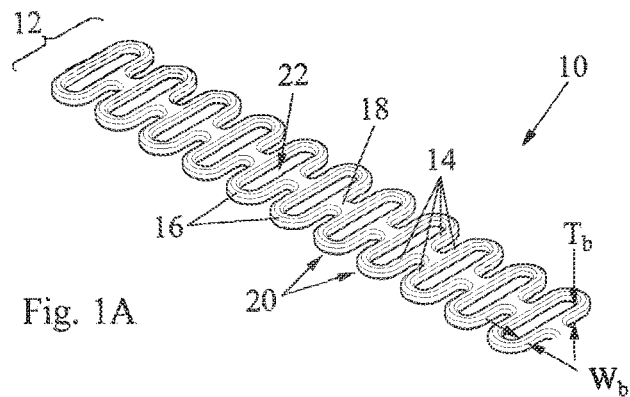
FIG. 1A is a partial perspective view of an example embodiment of a single spring member layer.
Figure 1B:
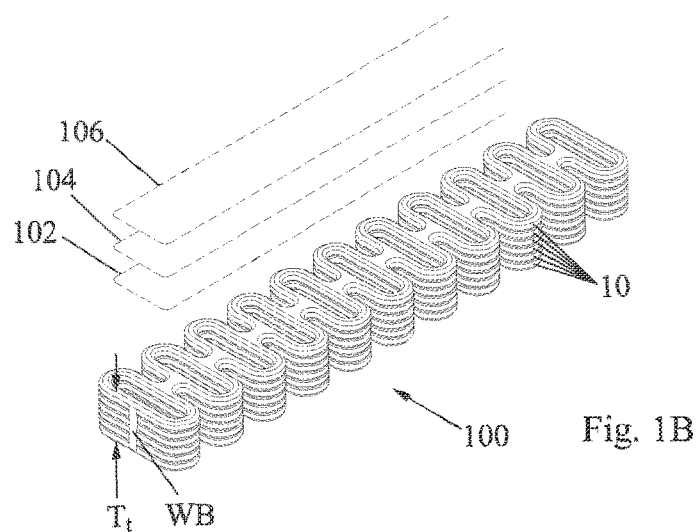
FIG. 1B is a partial perspective view of an example embodiment of a construct made with multiple layers as shown in FIG. 1A.

FIG. 1A shows an example embodiment of a single layer 10 (can also be referred to as a body, or constituent body or part), that may be stacked to produce or define a spring member construct 100 as shown in FIG. 1B. As mentioned already (and described in greater detail herein), implant embodiments utilizing spring member construct 100 have dramatically and unexpectedly improved fatigue life as compared to one-layer spring members that are otherwise similar or comparable in overall thickness.

As shown in FIGS. 1A and 1B, layer 10 is in the form of a stretchable or spring-type architecture that includes multiple beams or beam members 12. The beams 12 each include a lateral bar or beam component 14 free to deflect for stretching the spring member layer 10 axially. The lateral bars 14 are provided in opposing pairs joined to each other at an outer extent connector 16 of each beam. Stated otherwise, layer 10 can include a plurality of beams 12 arranged in pairs, where a first beam and a second beam of each pair are connected to each other only at the two lateral outer extents 16 such that the first beam opposes the second beam. Each connector 16 may be a curved continuation of each bar 14 or beam 12 or otherwise configured. Each pair of beams 12 is connected to an axially adjacent pair by a medial connector or bridge 18. As such, gaps are present at the two lateral outer extents between each pair of beams and the adjacent pair of beams as shown. The beams 12 or beam pairs serve as leaf spring elements in series that are arranged in cells 20, each with a central window or aperture 22.

The shape of these (integral or integrated) elements may present as a race-track configuration as shown. Within the same basic description above, the various beams, bars and connectors may be configured in substantially rectangular, oval, circular or other configuration (e.g., including more complex aspects such as stress-relief features as shown FIG. 4B of U.S. Pat. No. 10,194,946 referenced above, as described in connection with FIGS. 9B and 9C below, or otherwise).

Regardless, an overall spring member or multi-layer spring member construct 100 is shown in FIG. 1B. It may include a weld or weld bead (WB) at either end (only one end shown, although both ends may be welded). The weld bead or seam may be placed as shown to capture all of the layers or elsewhere with the same result. In any case, the welding serves to keep its individual or otherwise-independent layers 10 together for ease of handling until anchor application and after any trimming after anchor final position is set. Alternatively, a preloaded anchor or button at one end (of the same type described or another configuration such as a welded-on all metal button) can hold the pieces or elements together. Still further, the layers may be adhered, brazed or pinned together, swaged within a ferrule or hypotube, or secured within a length of heat shrink tubing.

Whether provided by a weld, multiple weld spots or otherwise, the connection between layers will typically be located in a region that can be trimmed off the implant and discarded once sized. The layers of the final (i.e., trimmed configuration) spring member portion of the implant will generally only be secured or coupled (with anchoring heads or an attached foot and an anchoring head) at their respective ends. As such, the individual layers can work in a parallel spring arrangement, yet failure of one layer (e.g., due to cyclic fatigue) will not affect the performance dynamic of the others.

That being said, an implantable sheath may be used in the subject systems (e.g., as described in U.S. Pat. No. 10,194,946). This sheath may surround and keep the spring member layers together within a given profile or envelope, but it will generally not lock them together or couple them along their length.

Layers of a given thickness (generally—although not necessarily—of the same thickness as shown) can be stacked to define a thicker implant when additional axial force capability and/or a higher spring rate is required. Three such optional additional layers 102, 104 and 106 are shown in dashed line in FIG. 1B. Conversely, fewer layers may be stacked in a thinner implant for indications where less compressive force is desired. In general, at least two or more layers, and preferably at least three or more layers are used for the sake of redundancy in the event of failure of a single layer per the logic described above.

As shown in FIG. 1A, a ratio of beam member 12 thickness ($T_b$) to width ($W_b$) in each layer may be about 1:1. This ratio may be relatively smaller or larger, for example, from about 2:3 to about 3:2 and still achieve fatigue advantage.

In terms of absolute dimensions with respect to the, for example, NiTi material examples described herein, beam thickness may be about 0.01 inches (0.25 mm). More particularly, it may be between 0.008 inches (0.20 mm) and 0.012 inches (0.30 mm) thick. Further variability is possible as well. For example, three-layer spring member bodies may prove to be fatigue resistant (as well as offering some redundancy in the event one layer fails) with layers between about 0.013 inches (0.33) to about 0.015 inches (0.4 mm) thick. With the benefit of the present description, those of skill in the art can arrive at comparable dimensions for other materials as well.

Example System or Device Embodiments

Figure 2A:
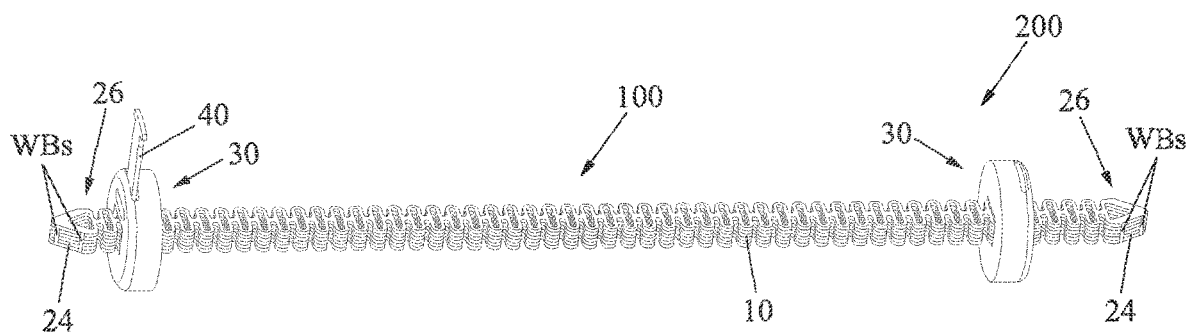
FIGS. 2A-2C are side perspective views of example embodiments of complete orthopedic implants or surgery systems with spring members layers as shown in FIGS. 1A and 1B.

FIG. 2A shows a first overall device or system or embodiment 200. In this embodiment, two opposite-facing anchor or anchoring heads 30 are used in associated with spring member 100. Alternatively, the anchoring heads may be referred to as buttons or button-anchors. The spring member 100 in this embodiment 200 may include the addition of tabs 24, each defining an eyelet 26. A similar tab feature is disclosed in U.S. Publication No. 2019/0046253 and PCT Publication No. WO 2019/032231 for tying on or otherwise securing an associated introducer (or "Beath") needle with a length of suture or other cordage. As such, only one such tab/eyelet feature need be used in the device 200, but both may be included for ease of manufacture and/or welding purposes. FIG. 2A also shows the manner in which multiple individual tack weld beads (WBs) may be used to secure the layers (in the case of this embodiment 200, six such layers) to one another.

In use, the needle is passed through a clearance hole drilled in bone and used to pull the spring member therethrough. The leading end of the device self-centers relative to the bone tunnel through which it is passed when given the triangular shape of the associated tab and eyelet. Finally, tab(s) 24 is/are trimmed off together with any associated extra length of the spring member 100 that is remains upon securing the anchoring heads after any desired tensioning. As in the above-referenced patent and patent applications, such trimming may be accomplished with a flush cutter, a custom tool or otherwise.

Figure 2B:
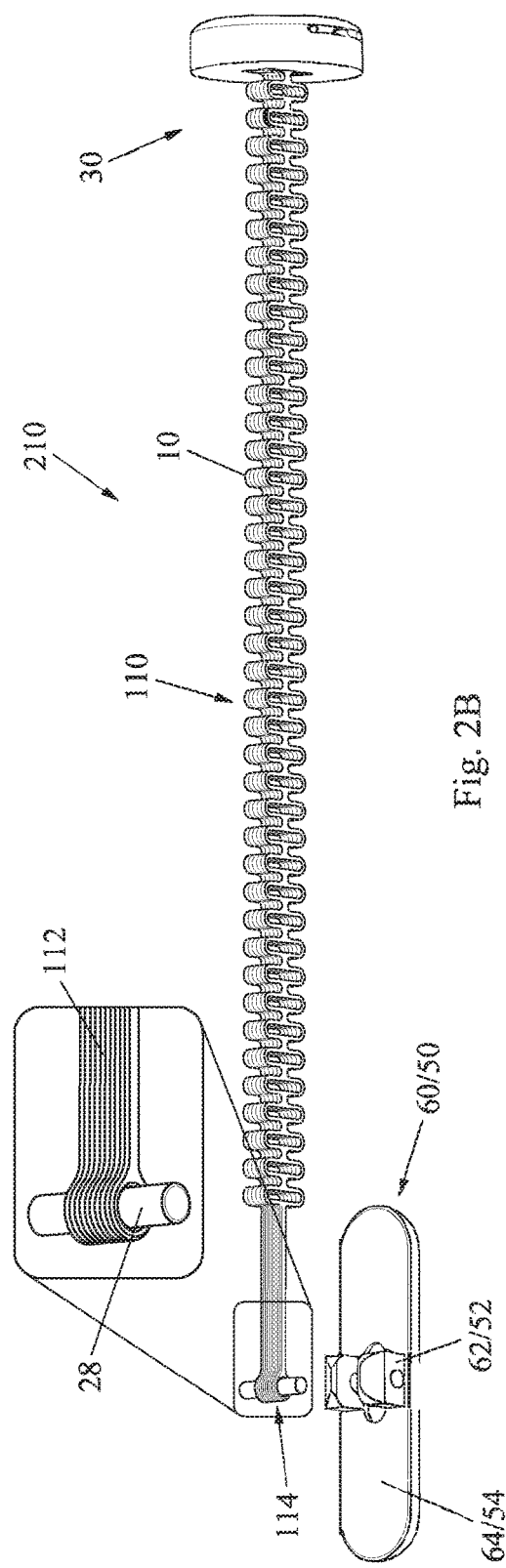

FIG. 2B shows second device or system embodiment 210. It includes one anchoring head 30, optionally as above, and a pivoting foot anchor 60 at the end of the spring member. Specifically, embodiment 210 includes a straight, axial or longitudinal extension 112 from each layer 10 in the spring member section 110. Each layer's extension includes a terminal eyelet 114. A single cross pin 28 is received through the eyelets and received in opposing bosses 62 of the foot anchor. A press fit may be employed to hold the pin in the bosses. This approach offers both simplicity and a given orientation of the anchoring foot relative the width of the spring member body.

Figure 2C:
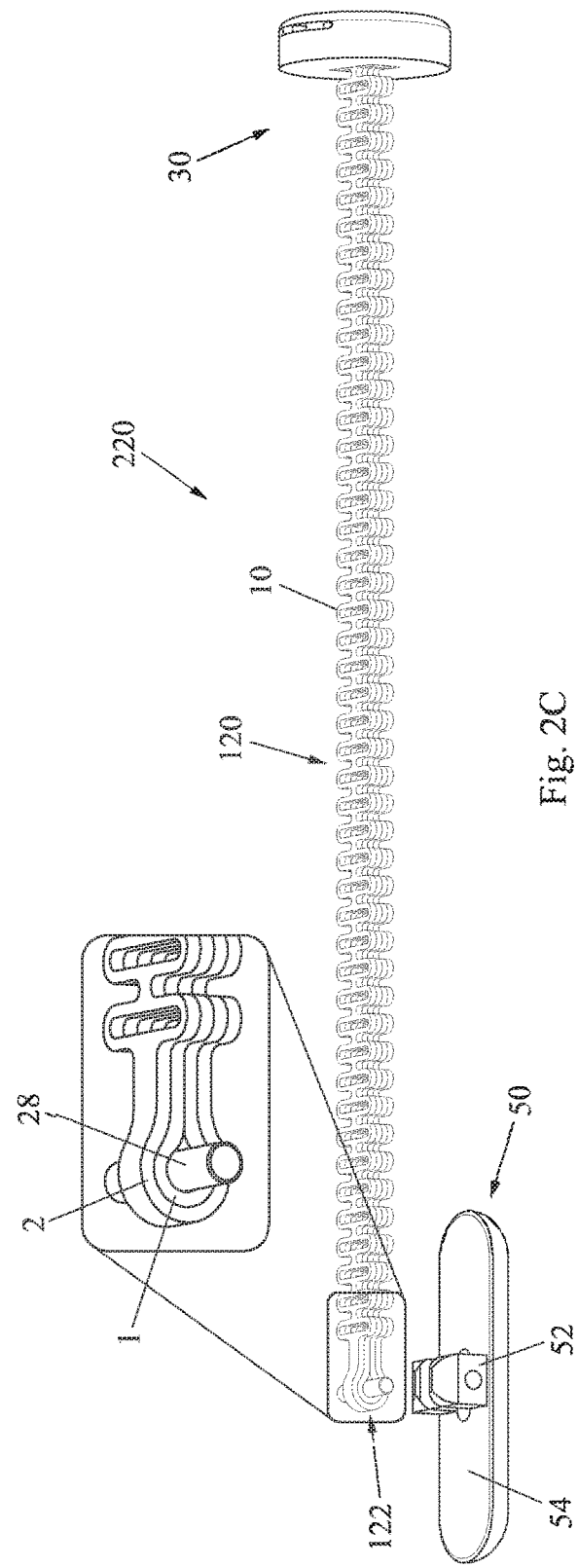

FIG. 2C shows a third device or system embodiment 220. Like the embodiment in FIG. 2B, one anchoring head 30 and a rotatable anchoring foot 60 is used. In device 220, however, the orientation of the body 120 to the anchoring foot is rotated by 90 degrees.

Such an orientation may be desirable for treating certain indications. Additionally, with a face 64 of its anchoring foot 60 stowed flat against its spring member body 120, system 220 can be configured to pass through a slightly smaller pilot hole though bone than system 210 with its orthogonal body/foot orientation.

It is also notable that pattern of cells 20 in spring member 120 may extend nearly to the pivot pin 28 of the anchoring foot. This may be advantageous in maximizing the active length of the device (e.g., in the examples provided, system 220 includes 5 more spring member cells 20 that in system 210). For a given amount of axial displacement required of the device, a longer active length (or stated otherwise, a greater number of otherwise identical cells within a given length) will reduce the strain in each cell thereby offering the potential for further fatigue life improvement.

For construction, the material layers 10 that define the spring member layers in system 220 are bent over and heat set (e.g., at about 500 degrees Centigrade for about 5 minutes in a furnace or lesser time in a salt bath) in the folded form to define a sort of stirrup at a fold 122 to receive the pivot pin for foot attachment. The stirrup may be a simple "U" shape. However, the "C" or "lightbulb" shape show is desirable for the purpose of capturing pin 28.

In embodiment 220, two parts or pieces (1, 2) are folded over to form four layers 10 in the spring member section 120. Alternatively, one folded-over piece may be used to provide a two-layer spring member, or three folded over pieces may be used to provide a six-layer spring member and so forth.

Each of the pinned-on-foot embodiments of FIGS. 2B and 2C are advantageous in terms of their robust connection and ease of precision manufacture. So-connected or affixed, the anchoring foot 60 can rotate from a position aligned with the spring member body 110/120 to a position transverse (or at least angled, typically upwards of about 45 or about 60 degrees up to 90 degrees) to the spring member body for anchoring (typically, the distal end of) the overall device during a medical procedure.

Complicating features (e.g., means providing a bias towards the transverse position by an integral or a supplemental spiral spring to aid transition from the foot's axial delivery configuration to its implanted position) may also be provided. Alternatively, one or more pull wires or cords may be employed to accomplish or assist with such rotation. Other deployment system options applicable hereto are presented in U.S. patent application Ser. No. 16/728,851, filed Dec. 27, 2019, titled "Bone and Joint Stabilization Device Features and Delivery Systems."

Figure 12A:
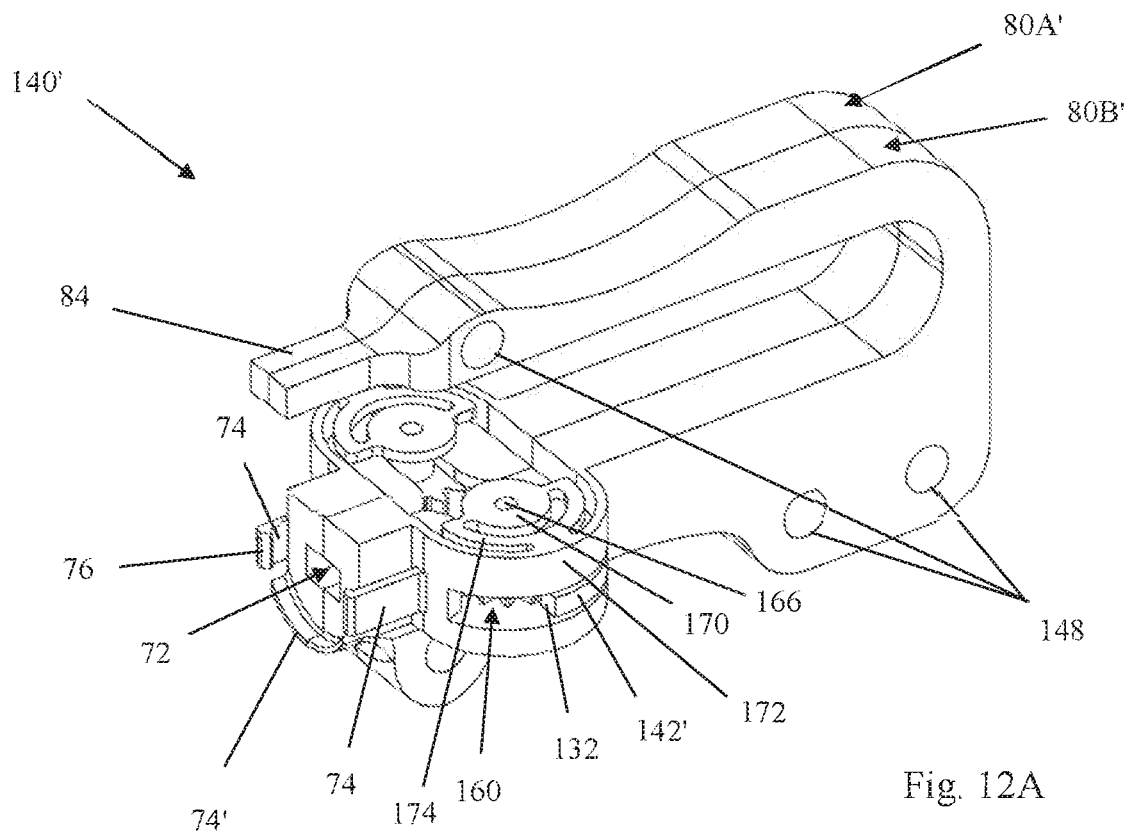
FIG. 12A is a perspective view of anchor loader embodiment that includes detented gears.
Figure 12B:
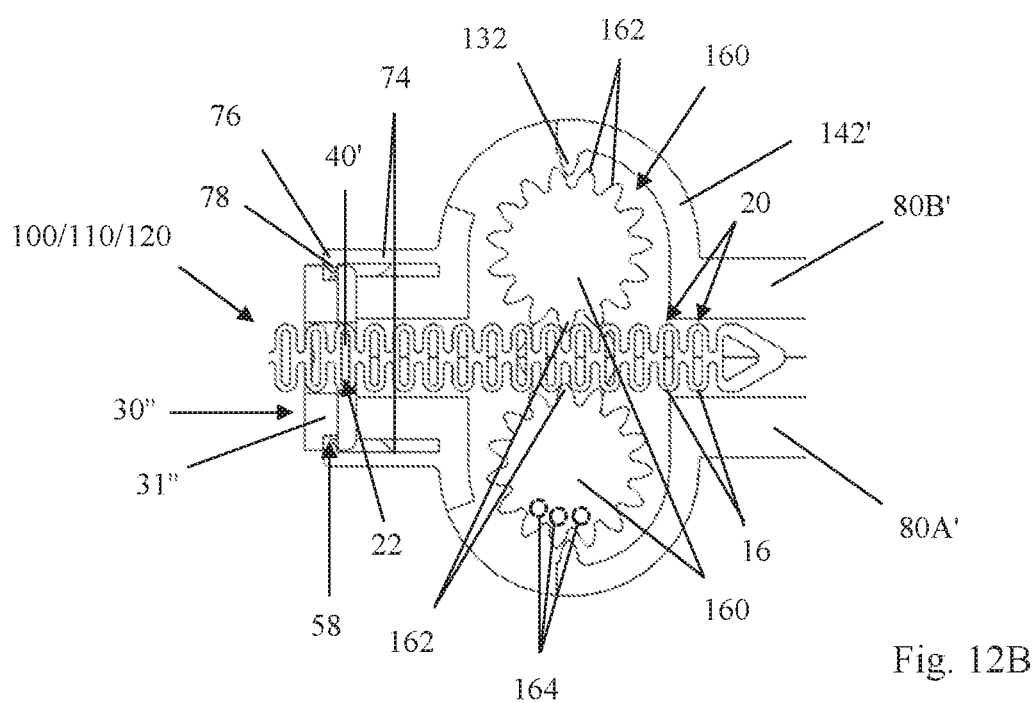
FIG. 12B is a bottom cross-section view of the anchor loader of FIG. 12A with the addition of anchoring head and spring member portions.

Conversely, the multi-layer spring member components described herein may be used in the systems shown and described in the Ser. No. 16/728,851 application. Examples of such systems include devices tipped with bone screws and various needle configurations. Independent of such details, the construction techniques (e.g., laser cutting a specific flat pattern (such as shown in FIGS. 12A-12C) or injection molding similar pieces) and material selections (e.g., Nitinol or beta titanium alloy for the spring member body layers, poly-ether-ether-ketone (PEEK) or polyetherimide (PEI) polymer material for the anchoring head and/or foot, stainless steel for cross-pins, etc.) described in that application as well as the other patents and patent applications incorporated herein by reference may be used in the subject embodiments as well.

Anchoring Head or Button Embodiments

In the anchoring head embodiment 30 shown in FIGS. 3A-4B, a body or base 31 of the anchoring head may be made of PEEK or another biocompatible polymer. It may be machined, molded or 3D printed by fused filament fabrication (FFF) or selective laser sintering (SLS) or other means. The polymer may be loaded with radiopaque material such as barium sulfate for radiopacity.

Alternatively, body or base 31 may be made of titanium, titanium alloy or stainless steel to be fully radiopaque. For such purposes, the part or piece may be 3D printed by SLS. This may be desirably from the standpoint of providing optional complexity (e.g., as with included detent features as described below), especially given the small size of the part and its features.

A tooth 40 to catch or hold the spring member within the anchoring head body or base 31 may be made of metal. Such a tooth offers strength and radiopacity when made of either stainless steel or Nitinol. A Nitinol tooth may be advantageous to limit the possibility of bi-metallic corrosion with the Nitinol spring member. Also, it may give more flexibility of design to include detent features by allowing greater deflection for incorporated elements.

FIGS. 3A and 3B show anchoring head body or base 31 before crossing tooth 40 and spring member 100/110/120 insertion therein. The tooth piece, which can alternatively be referred to as a (flattened) cross-pin or cross-member, includes a spanning portion or section 42 and a deflectable latch in the form of optional hooks or nubs 44 carried on flexible arms or bars 46 that can deflect inwardly (e.g., horizontally or side-to-side relative to the bottom or underside "U" of body 31) when the tooth is inserted into a cross-channel, track or tunnel 32 defined in body 31. When overhang sections 48 of the tooth abut stop sections 33 in body 31, the nubs 44 lock within complimentary sockets, pockets or recesses 34 as shown in FIG. 4B.

FIG. 4A illustrates the first stage of such insertion with the spring member body 100/110/120 received through a transverse clearance hole or feed opening or aperture 35 in the anchoring head body or base 31. FIG. 4B is a cross-sectional view taken along the midplane of cross-channel 32 and depicts the fully inserted or locked position of the tooth 40 relative to the anchoring head and a multi-layer spring member 100/110/120. Positioned thus, each of the layers of the spring member body is securely held with tooth portion 42 passing through the window 22 within each engaged or captured cell 20 of the multiple layers (their connector portions or segments 16 seen in cross-section).

The tooth is advantageously carried by or incorporated in the anchoring head before use. Stated otherwise, it is optionally received within the anchoring head such that it cannot back-out or otherwise inadvertently separate therefrom prior to tooth advancement or deployment to cross and hold the spring member layers. Recesses 36 serve as detent features for such purpose. These receive hooks or nubs 44 and allow their release when the tooth is pushed fully into the anchoring head. The recesses in channel or track 32 may be formed by drilling (or molding) the part as shown in FIG. 4A with cross holes 37.

Other anchoring head base and tooth configurations (with their incorporated stops and detent features) are possible as well. For example, the flat surface of the tooth may include one or more bumps that interface with holes 37 for detent capture and release. The tooth may include first and section (e.g., hold and lock position) bumps for this purpose. Alternatively, additional detent holes may be included in body or base 31 for a single bump on the tooth surface, or even its side(s). Yet another option is to form a hole in the tooth and set a ball (e.g., made of PEEK or another plastic, elastomer or stainless steel) in that hole to interface with one or more detent-completing holes in the base.

Another such detent approach is shown in connection with the anchoring head 30' configuration shown in FIGS. 5A and 5B. Here, a slidable tooth or cross-pin 40 includes a deflectable latch in the form of a flexible tang(s) 46' that can move up-and-down relative to the flat underside U of the anchoring head when passing through channel 32. Ends 44' of each tang will lock when received in a pocket or receptacle 34' formed in the anchoring head body. As for the detent feature, is provided by the interaction of tangs 46' in association with pocket or cavity 36' machined or molded from above (e.g., as illustrated in connection with slot 37').

Aside from the advantages of incorporating optional detent feature(s), the important aspect of the anchoring head design involves the sliding receipt of its tooth within the base. This configuration enables passing the end of the tooth completely through and past the multiple layers in the spring member. Positioned thus, all of the spring member layers 10 are directly supported or held by the spanning portion 42 of the tooth.

Figure 8:
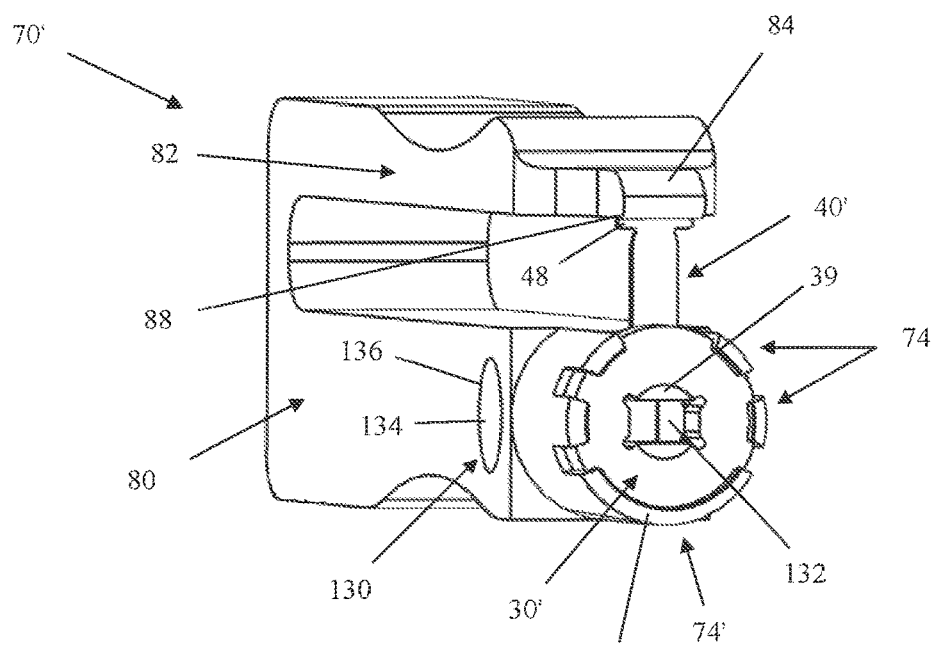
FIG. 8 is a perspective view of another example embodiment of an anchor loader, with an anchor received therein.

While it is important that spanning portion 42 supports or holds each of the spring members layers 10, it is also important that the spanning portion of the crosses or spans the spring member feed opening or aperture 50. Such an arrangement offers support to each side of the tooth, providing strength to the interface. Optional chamfer or lead-in features 39 (illustrated in dashed line in FIG. 5B) for spring member receipt that may be machined or molded into the body or base 32 are also useful. These features may take the form of angles surfaces as indicated in FIGS. 5B and 6B or they may be curved or cup-shaped features as shown in FIG. 8.

In any case, FIG. 6A is a perspective view of an upper or outer body piece or portion 31A of another anchoring head example embodiment. FIG. 6B is a perspective view of a lower or inner body portion 31B of the same. When connected, they form a body 31" for an anchoring head 30" as shown (in cross-section) in each of FIGS. 11B and 12B.

Such connection or attachment may be made by an interference fit between pegs, posts or pins 50 within sockets or pockets 51 (or through-holes) in part 31B. Or the pins may be carried by body 31B and the sockets or through holes made in part 31A. Either way, the pins may be round, hexagonal or D-shaped as shown to include flats for air to pass out of the sockets (shown) during a press-fitting procedure.

Body piece or portion 31A includes a spring member feed opening or aperture 35 and a slot 32' that defines a closed the channel when body portions 31A and 31B the parts held together. Body piece or portion 31B also includes a feed opening 35 that aligns with that of its complementary piece. In addition, body 31B includes one or more pockets or troughs 52 to receive the deflectable latch portion of the tooth to be used.

Each such pocket may serve a purpose comparable to 34/34' and 36/36' in the previous embodiments. Symmetrical shape and/or placement of pockets 52 can be of assistance for assembly (making the part non-directional with respect to the slot 32).

Figure 11A:
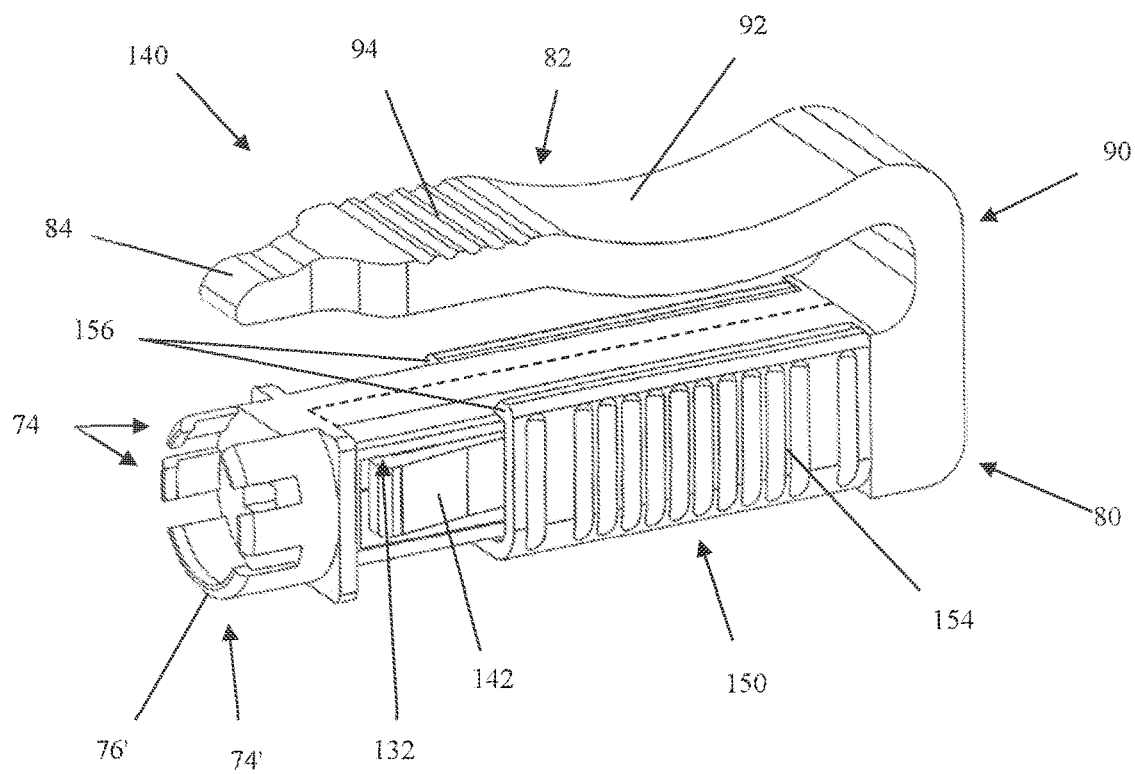
FIG. 11A is a perspective view of anchor loader embodiment that includes active detent features and a locking collar.
Figure 11B:
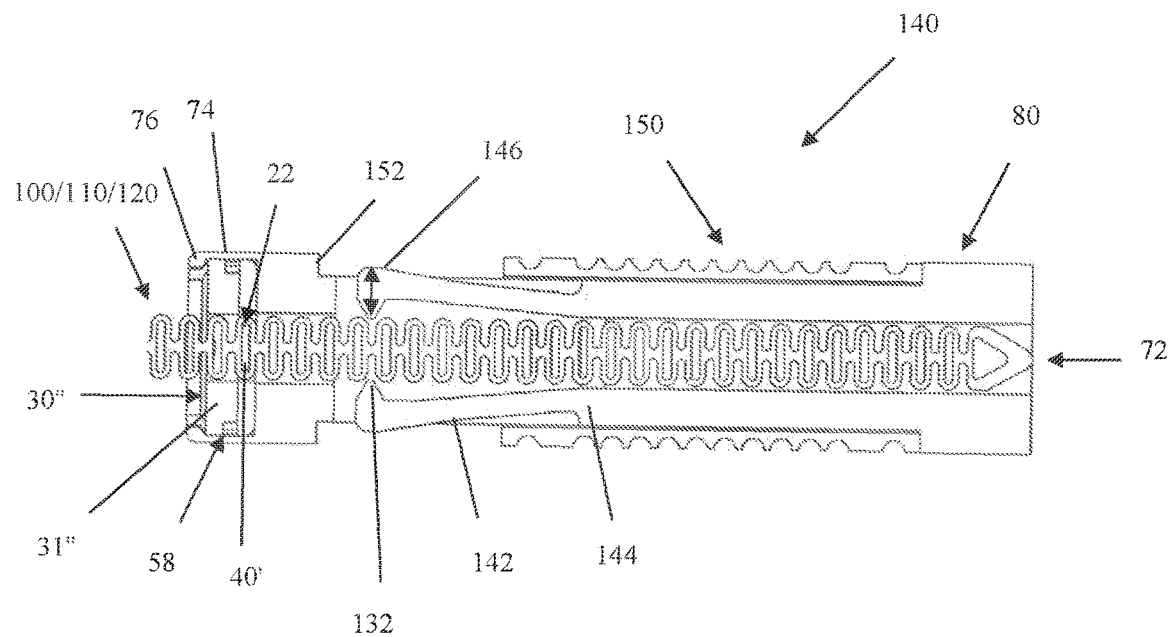
FIG. 11B is a bottom cross-section view of the anchor loader of FIG. 11A with the addition of anchoring head and spring member portions.

In another optional aspect, either one (or both) of pieces 31A and 31B may include an side-cut region 54 to produce a ledge 55 to define opposing side slots 58 (as shown in FIGS. 11B and 12B) for holding the anchoring head apart from a base when the pieces are assembled (i.e., held together). A ramp section 56 may also be included to ease anchor loader removal.

The base or underside (U) of part 31B may include a spring member lead-in section or sections 39. These may be chamfered surfaces as described for anchoring head(s) above or may be shaped as a concave or cupped set of surfaces as with the anchoring head 30' shown in FIG. 8.

Figure 7A:
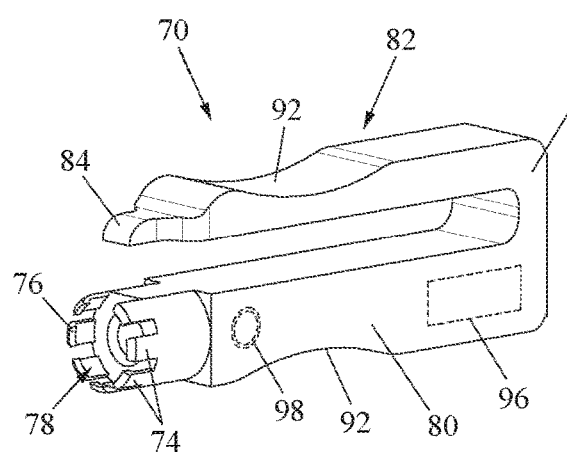
FIGS. 7A and 7B are different perspective views of an example embodiment of an anchor loader for coordinated use with the anchoring heads detailed in FIGS. 3A-3B and 5A-5B.
Figure 7B:
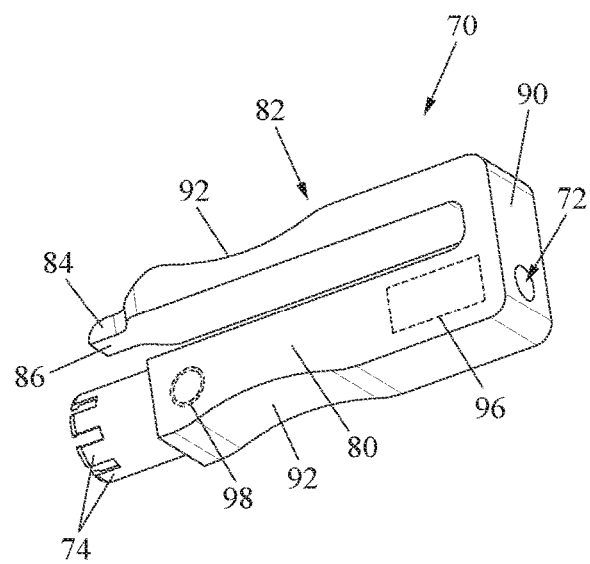

To facilitate handling and use of the anchoring heads as further described below, an anchor loader and pin/tooth pusher device may be desired. FIGS. 7A and 7B detail such a device. It is modified from related loaders shown in FIGS. 9A-11D of U.S. patent application Ser. No. 16/728,851 by the addition of a pin-pusher lever arm or beam as shown.

More specifically, a plunger-style loader or loading tool 70 includes a tunnel or through-hole or bore 72 to allow passage of a spring member body. It also includes a plurality flexible extensions or "fingers" 74 with overhanging catch portions or tips ("nails") 76. An undercut ramp section 78 of each tip to allow anchor release when desired by pulling the loader off the anchor once its position is set and anchor locked. The fingers are narrow and thin enough to allow the necessary flex to accommodate such action. Eight independent fingers are shown, but as few as three (typically symmetrically disposed) may advantageously be employed.

The handle or body portion 80 of the plunger may be box-shaped or otherwise configured (e.g., rounded or round). A lever arm 82 is connected to the body. It is able to flex toward the body 80 and includes a reduced-width and/or radiused tip 84 configured to push a tooth received in an anchoring head with surface 86. The connection 90 between body 80 and lever arm 82 may be configured to serves as a so-called living-hinge. Inset grip or location positions 92 may be included in each feature.

Figure 9A:
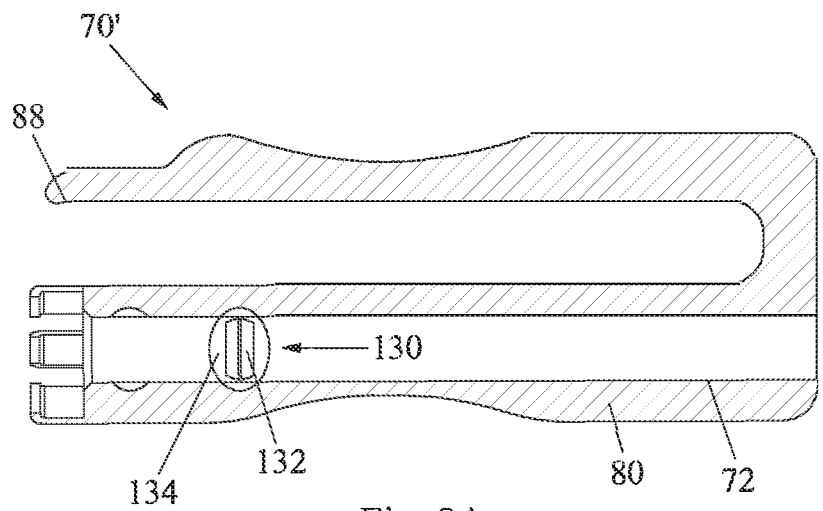
FIGS. 9A and 9B are side cross-section views of the anchor loader shown in FIG. 8.
Figure 9B:
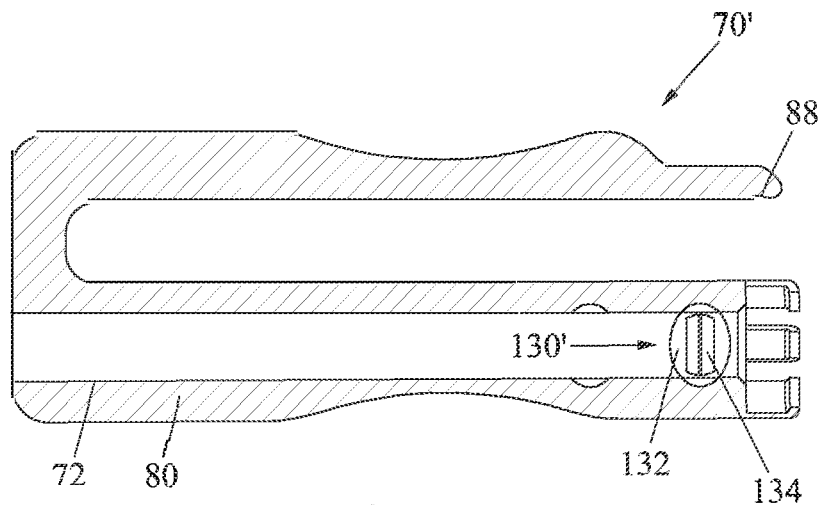
Figure 10:
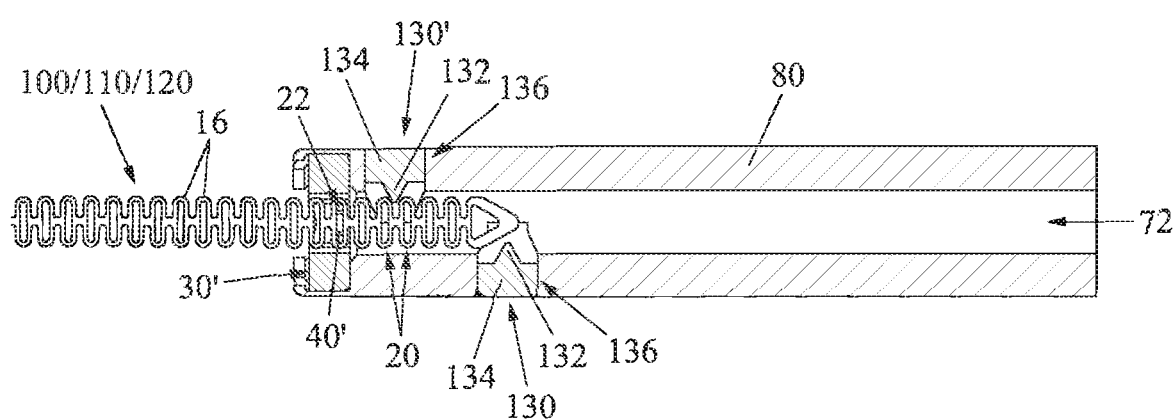
FIG. 10 is a bottom cross-section view of the anchor and anchor loader shown in FIG. 8 with the addition of a spring member.

Additional optional features are pictured in the anchor loader embodiment 70' show in FIG. 8 (holding anchor 30') and further detailed in the cross-sectional views of FIGS. 9A and 9B (without the anchoring head). FIG. 10 shows the same system in cross-section with a spring member body 100/110/120 received within an anchor 30' held by the anchor loader 40'.

Regarding the subject features, lever arm 82 includes a notch or grove 88 formed to stabilize the crossing tooth 40' during insertion. The groove may be straight, or radiused to match the curvature of the end(s) 48 of the tooth (which are themselves so-configured to match the curvature of the body 32/32' of the anchor). In addition, loader embodiment 70' is configured to provide indexed operation in connection with the spring member body received therein.

Such action is accomplished in connection with detent features. In one example embodiment, each of inserts 130 and 130' include an inwardly-directed protrusion 132 that interacts with the sides or end connectors 16 of the spring member body to be received in the loader. This relationship of elements is shown in FIG. 10.

Here, "V" shaped protrusions 132 are provided. These seat or nest between adjacent cells 20 when the body 100/110/120 is pushed or pulled through the anchor loader 70'. The angle of the V, the size of any radius or flat at the peak of the V, and length of inserts 130 and 130' (and thus the depth of the protrusion) can be configured such that a positive engagement is felt (e.g., a tactile response is felt). In this embodiment, protrusions 132 act as detent features, and the response is felt as the spring member flexes as a cell 20 of body 100/110/120 passes over a protrusion 132 such that the protrusion 132 comes to rest in stable equilibrium position in the gap between adjacent cells 20. In such an arrangement or configuration, the spacing between the detent features and the anchor received in the loader is such that when in such position, the crossing tooth or pin 40' of the anchor is aligned with a "window" 22 of the spring member ready for successful deployment.

As such, the convenience of this feature is notable. Within the solution, the use of two detent features (or more) is also optional. However, it can work with one and, thus, a single insert.

Further, the orientation of the detent features (or simply, "detents") may be changed. For example, it (or they, if plural) can be set in a perpendicular plane relative to those described so that the interaction with the spring member is with its face and windows 22 instead of along its side as depicted in FIG. 10. In this case, it may be advantageous for the insert(s) to be flexible (e.g., using a NiTi alloy "card") because entry and exit of the windows involves interface with square edges (whereas the spring member may be rounded—as shown—which naturally eases the transition or translation of the spring member relative to the detent features).

As for the configuration of the insert(s) defining the detent features shown, a base 134 to fit in a corresponding socket(s) 136 produced in the loader body may be oval in shape to guide the orientation of the V-shaped extension 132. Otherwise, the insert base may be cylindrical and orientation handled otherwise (e.g., by a slot for indication or turning the insert like a screw head).

The apparatus is this embodiment relies on spring member flexibility (and bore 72 clearance within body 80 to allow for flex) to provide spring action over the detent features. Thus, in the embodiment, the loader 70' does not include a discrete spring member on which the inserts 134 are mounted or ride that would otherwise permit back-and-forth sliding motion as the cells 20 move past the protrusions 132. However, in alternative embodiments, loader 70' can include a spring or other bias member that permits back and forth motion of the insert 134 or protrusion 132 itself. Stated otherwise, the detent itself may be spring-loaded. Still further, the shape of the detent can vary as may be the material from which it is made. Stainless steel, NiTi, PEEK or another material may be selected.

A difference between embodiments 70 and 70' is shown in connection with the so-called fingers 74 and 74'. In loader 70' those fingers 74' opposing the downward push of lever 82 and the crossing pin or tooth 40' are joined together. Stated otherwise, a partial cup 74' is provided in embodiment 70' that may include an overhanging catch rim 76' as shown.

The body of anchor loader and/or the inserts may be injection molded or machined for manufacture. The body of the anchor loader may include a textured surface or additional features for user grip where handled. Preparing the device for use (i.e., inserting an anchor into the loader) may be done manually by a user or it may be done in advance such that the anchor and loader or plunger are provided in "kit" fashion.

Returning to FIGS. 6A and 6B, the anchor loader (whether it includes the detent features described or not) may include an optional (as indicated by dashed line) meter or counter 96. It may use a flap or a spur-gear mechanism internal to body 80 that interfaces with the windows or apertures 22 of the body fed therethrough. In use, the end of the loader is advanced until anchor contact with bone or a plate with which it will be used. Then, either 1) an optional button 96 may be pushed to engage the flap or spur gear with the body, or 2) the button is pushed to zero-out the meter or counter 98.

As a counter, it may indicate the number of cells (by counting windows or apertures) pulled to tension the body. As a meter, it may display a tension or compression force estimate. This is possible in the situation when the loader (or overall system) is selected for an expected active length of the spring member between the anchors—a matter that can be ascertained under x-ray or using a calibrated C-clamp or a customized measuring tool.

The readout may be use analog counter wheels, an analog type of scale or a digital counter or display. Moreover, while simple mechanical means (e.g., a flap or spur gear) have been disclosed to interface with the body 100/110/120 to count cells or estimate tensioning, electrical (analog or digital) means may instead be used.

FIG. 11A is a perspective view of anchor loader embodiment 140 that includes active (i.e., spring-loaded) detent features and a locking collar 150. FIG. 11B is a bottom cross-section view of the anchor loader of FIG. 11A with the addition of an anchoring head 30" shown and a portion of a spring member 100/110/120. As seen in each view, a detent tooth or pawl 132 is provided (e.g., integrally formed) at the end of a lever arm 142 extending in cantilever beam fashion from a junction 144 with the rest of the anchor loader body 80. The subject embodiments may include two such detent features as shown or may be one-sided in design.

As for their action, it may be desirable to inset each detent pawl so that tactile feedback is produced in passing the spring member past the same. For example, 0.003 inches worth of inset (interference) may be desirable when the loader is produced in Nylon, PEEK or another engineering plastic. So-configured, inward and outward motion (with associated tactile resistance) is experienced as indicated by the double-headed arrow in shown in FIG. 11B.

Whether or not such an approach is selected, the lever arm(s) include a hump or ramp 146 to be pushed inward upon advancing sleeve 150 toward and (optionally) past pawl 132 into contact with a stop region 152 of body 80. In this position, the anchor tooth 40' is aligned with an opening 22 of the spring member body for deployment therethrough.

Grip features 154 may be provided along the sleeve from an ergonomic perspective. Clasp features 156 may hold the sleeve on body 80. For assembly, the pieces may simply snap-fit in place.

For manufacture, body 80 may be provided as a single piece, especially if it is to be constructed using SLS or another additive manufacturing approach. For production by machining or injection molding, the body may be produced in two or more pieces that can be press-fit or snap-fit together, or secured with fasteners (e.g., as described with respect to loader 140' described below). The dashed separation or parting line indicates one such option for how sub-component pieces of the body may be configured (in part) and ultimately fit together.

Figure 11C:
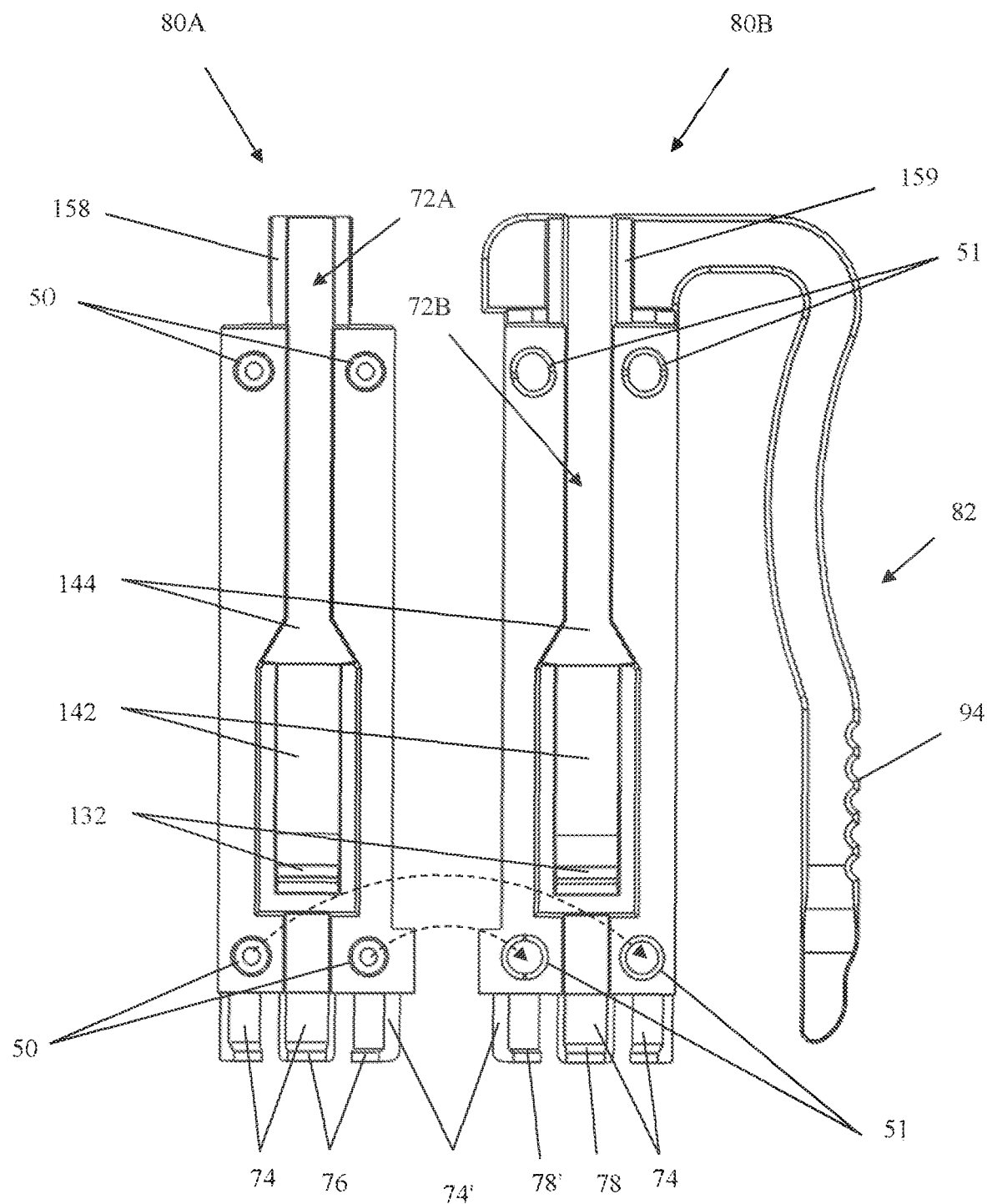
FIG. 11C is an assembly or construction view of parts of the anchor loader embodiment of FIG. 11A configured for machining or injection molding in two parts.

FIG. 11C details a configuration of the anchor loader 140 body comprising separate body parts 80A and 80B. Such an approach is designed for production by machining or injection molding. The pieces are assembled as indicated (by the arrows) employing a press fit between pins 50 and sockets 51. Stability of the fit between pieces 80A and 80B is also aided by the interface between a shank 158 and channel 159.

Another notable feature is the shape of the sockets. They may be asymmetrical in design to provide one round, tight fit (locating) pin/socket combination and three pins to be received in slot-shaped sockets for variance of the manufacturing process. As shown, the long axis of these slots all orient towards the locating pin/hole combination to minimize overly constraining the fit.

Once assembled, the main body of the device is configured just as shown in FIG. 11A (if ignoring the inclusion of draft angles as variously shown in FIG. 11C which may in fact be omitted when the two-part-body approach is setup for machining). However, the configuration of the so-called fingers and tips for holding the implant anchor may be different (as shown in comparing the components in FIGS. 11A and 11C). Not only is a so-called "cup" portion omitted from the parts in FIG. 11C, but fingers 74' are increased in bulk (resulting in higher stiffness) relative to fingers 74 and ramp angle 78' is reduced relative to ramp angle 78 in order to aid anchor retention by the lower fingers during tooth/cross-pin advancement while still allowing anchor release (albeit with a slightly higher release force when pulling the loader off of the anchor after deployment). Elimination of the cup may reduce molding and/or machining challenges when considering design for manufacturability.

Regardless of the details of the configuration, in use, a physician may pull tension on the spring member body 100/110/120 between a previously installed anchor and with the anchor 30" and/or tips 76 of the loader device 140 set against the subject anatomy or an orthopedic plate applied thereto. With the tension in the system, collar 150 may be translated forward thereby locking the detent pawl(s) 132 with the side(s) of the spring member between its end connections 16. So-locked, the physician may physically check the tension of the device and/or radiographically confirm desired reduction of anatomy between the system's anchors. If under tensioned, sleeve or collar 150 may be returned to its original position, the spring member tensioned further and locked again. Once the physician is satisfied, the lever arm 82 is actuated by a thumb positioned against grip 94 deploying the slidable tooth 40' across the anchor body 32" through the opening 22 of each cell 20 in the multi-layer spring member construct 100/110/120. Finally, excess spring member body length is trimmed off.

Similar operation is possible in connection with the anchor loader 140' shown in FIGS. 12A and 12B. However, this system includes gears that mesh with the spring member. While not shown, a lock may be incorporated as well.

As for the general approach with the gears 160, however, they have an advantage of rolling with the spring member in constant positive engagement between cells 20 on and between each side connector 16 therefor. The meshing between the gear(s) and the spring member can be smooth or moderated by detent features. In one example, the detent comprises a pawl 132 located at the end of a flexible lever arm 142' much like that in the previous embodiment, except that the pawl interacts with teeth 162 of the spur gear(s). In another approach, sockets or pockets 164 may be machined in the surface of the gear(s). These may interact will ball detent featured carried by or incorporated in device body features (not shown). In any case, the detent feature(s) may be spaced with the gear(s) to align any of a plurality of windows 20 in the spring member body 100/110/120 for anchoring tooth 40' receipt.

Other optional constructional details include a two-piece body construction with body halves 80A' and 80B' as shown in FIG. 12A. These halves may be secured to one another via press pins or screws received within holes 148. Such a construction is amenable to production via machining or molding. However, this embodiment 140' and the other described above may be produced using so-called rapidprototyping or 3D printing techniques including SLS, SLA or FFF. Indeed, operable devices has been so-produced by the assignee hereof.

Yet another optional detail concerns the manner in which the gears are secured within the device. In one approach, a gear axis 166 may be received within a socket tab 170 connected to a gear housing 172 by flexible arms 174. Such an arrangement allows for snapping the gear(s) into place directly, rather than inserting and then pinning (optionally via press-fit) them into place.

Also notable, the distal end of the loader may include "fingers" 74 with overhanging "nails" 76 that interface with the aforementioned optional side slots in an anchoring head. These may be configured as shown to engage opposing medial slots 58 in the anchor body 31". Alternatively, such features may be configured as in the previous embodiments.

Figure 13:
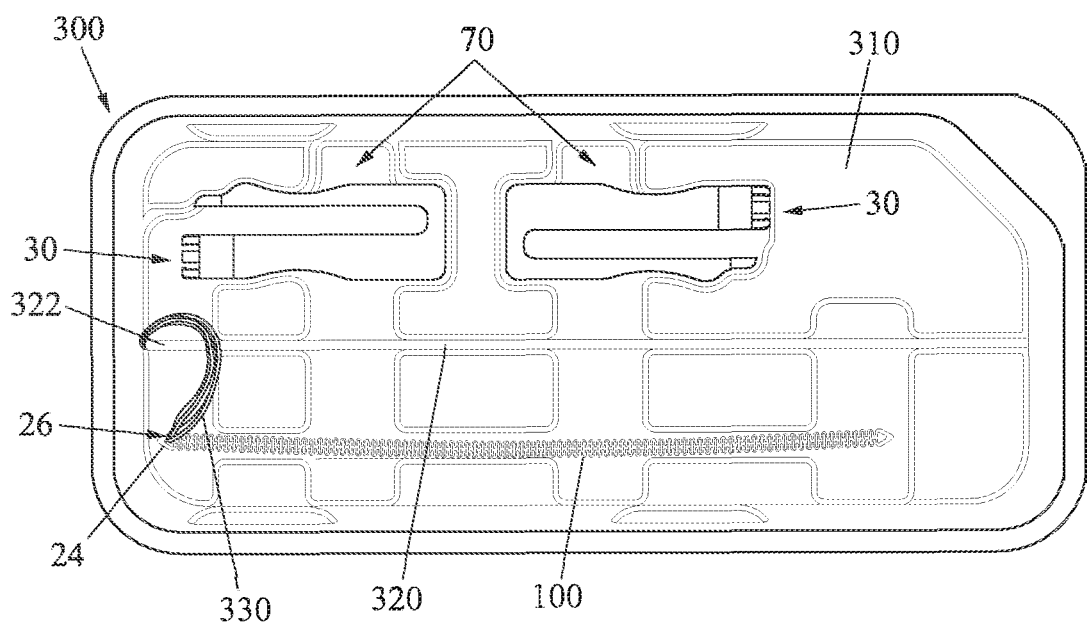
FIG. 13 pictures an example embodiment of an overall system with components selected from those variously illustrated in the figures referenced above.

Regardless of configuration, loaders 70 (or loaders 70', 140 or 140') may be pre-assembled or loaded with anchors 30 (or 30' or 30") and provided in a packaged combination or kit 300 as pictured in FIG. 13 in a thermoformed tray 310 which will typically be sealed by a TYVEK or another cover (not shown). The overall treatment system will also include a spring member 100 (or another such member 110 or 120). As discussed above, the spring member may be connected to a Beath needle 310 (or other introducer or guide). As shown, the needle is attached (through tab 24 and eyelet 26) using polyester suture material 320 received and held (e.g., by swaging) in a proximal end 322 of the needle.

Medical Methods

With an injury (e.g., a fracture or sprain) reduced to an anatomic position, one or more of the subject device embodiments is installed via incision(s) and pre-drilled hole(s). Tensioning may be achieved as a result of minor rebound of anatomy after it is manually compressed or reduced with a clamp with the device applied or installed as such. Alternatively, device tensioning may be accomplished as presented in FIG. 14 during which a modified version of a cable tie tool or so-called "zip-tie gun" may be used to automatically or semi-automatically tighten and/or trim the spring member body after tensioning. Such an instrument may include a spring-based force gauge or a digital force meter therein (additional details of the latter provided below) and an analog or digital indicator or light display (e.g., a green/yellow/red LED) to cue a user according to the method below.

Figure 14:
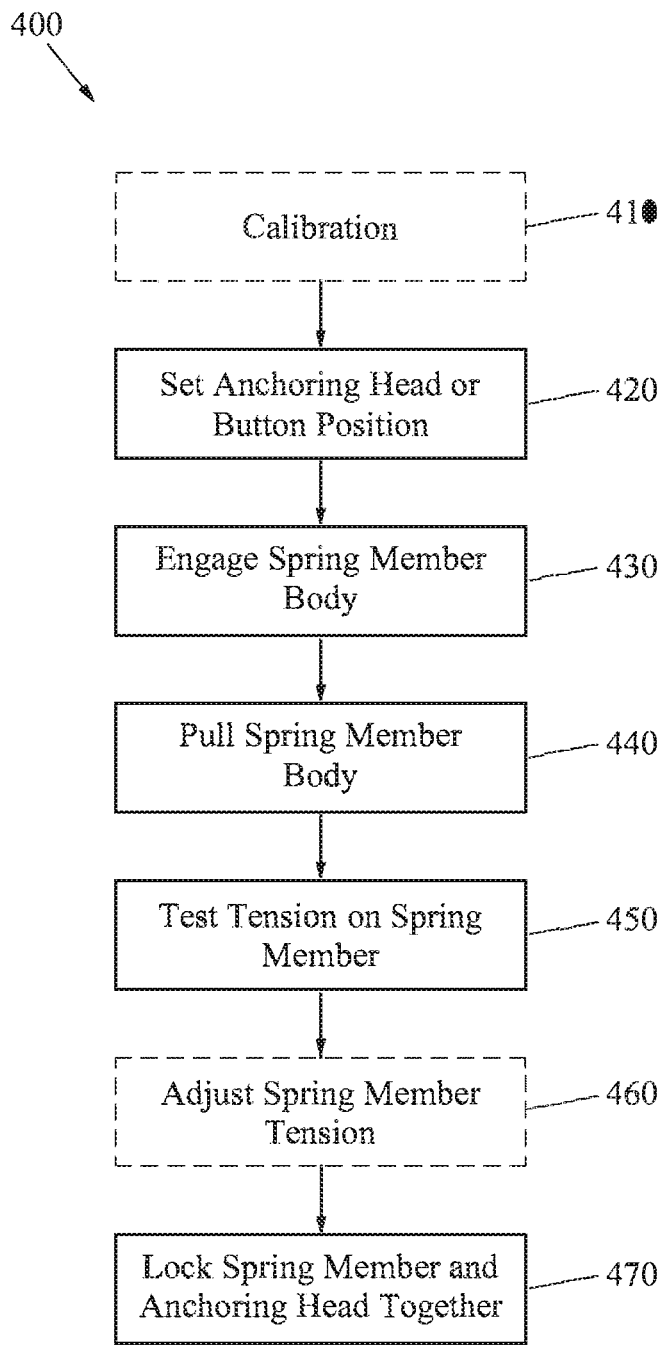
FIG. 14 is a flowchart for example tensioning method embodiments.

Referring specifically to acts or steps in the method 300 shown in FIG. 14, at 410 an optional calibration step may occur. This may be performed during manufacture on by the user intending to carry out the subject device or system tensioning method.

More likely, after distal anchor position is set (be it an anchoring head or anchoring foot, e.g. medially during a syndesmosis repair procedure) at 420, the proximal anchor position is set (e.g., laterally in a syndesmosis procedure). Then, at 430 the spring member is engaged or grasped (either by a surgeon directly, using forceps or a dedicated tensioning instrument). Alternatively, the order of these operations may be reversed.

Either way, the spring member body is pulled or retracted at 440. This provides or allows for a test of the tension on or applied to the spring member at 450. This test may be a relative or tactile test by the surgeon, but is preferably one quantified by digital or analog hardware as variously discussed.

If tension is not as desired, adjustment occurs at 460 by pulling in or letting out length of the spring member relative to the anchoring head. Whether or not optional step 460 occurs, the anchoring head pieces are locked together (e.g., with one of the sliding tooth and detent architecture described above) at 470.

Regardless of how preload application may be accomplished, excess spring member length is then be trimmed off (e.g., with flush cutters or a cutting jaws integrated in a tensioning device), leaving the remaining construct flush with the anchoring head. So-prepared, the subject devices remain active to provide continuous compression allowing for anatomical motion across a joint or provide a less stressful alternative to a stiff screw for a bone break. Finally, as referenced above, suitable methods of medical use also applicable to the present embodiments are described with respect to FIGS. 8-15 of U.S. Pat. No. 10,194,946.

Experimental Results

Cyclic fatigue testing and modeling results for a number of spring members and spring member components are presented below. The spring members were all laser cut (each with fiber laser technology) from superelastic Nitinol plate in the same flat or planform shape or pattern and electro-polished with about 0.001 inch material removal per side. Material thickness (together with any associated bulk material properties) in device production is therefore believed to be the significant variable in the comparison of cyclic fatigue life. Stated otherwise, efforts were made to provide a true set of comparisons below in testing device performance and making associated performance estimates.

Test Conditions A-D

A first set of testing is reported in Table 1 for samples categorized in terms of test condition type (Test Con.) A-D and considering Sample Type, Sample Overall Thickness in inches (in) and millimeters (mm), approximate Preload (Preload) applied to the sample(s) in Newtons (N) and gram (g) or kilogram (kg) force, Axial Displacement per cell 20 (Axial Disp./Cell) applied to the sample(s) in mm, Number of Cycles achieved (under noted conditions), and associated comments providing additional context. The unibody sample of Test Con. A was in the single layer configuration depicted in FIG. 1A but with a about a 5:1 aspect ratio of beam thickness (T) to width (W), with the thickness dimension noted in Table 1 below. The single construct layer of test Con. B was also in the single layer configuration of FIG. 1A with the thickness dimension noted in Table 1 and the 1:1 aspect ratio actually shown in the figure. The five layer construct samples of Test Con. C and Test Con. D were in the configuration of FIG. 1B (without additional layers 102, 104, 106) where each layer of the five layers had a 1:1 aspect ratio and the overall thickness of the five layers summed or totaled together (see $T_t$ of FIG. 1B) having the dimension in Table 1. The samples tested performed as follows:

TABLE 1

| Test Con. | Sample Type | Overall Thickness | Preload | Axial Disp./Cell | Number of Cycles | Comments |
|---|---|---|---|---|---|---|
| A | Unibody | 0.039 in 1.0 mm | 10N 1.0 kg | 0.028 mm | 17,100 (sample 1) 18,000 (sample 2) | Samples run to failure |
| B | Single Construct Layer | 0.008 in 0.2 mm | 2N 215 g | 0.028 mm | 1,665,000 (without failure) | 1/5 thickness of 1 mm Construct (preload scaled accordingly) |
| C | 5 Layer Construct | 0.039 in 1.0 mm | 10N 1.0 kg | 0.028 mm | 57,000 (1 layer failure) 1,728,000 (4 without failure) | Each layer in construct at 0.008 in/0.2 mm (same as in Test B) |
| D | | | | 0.042 mm | 36,500 ($2^{nd}$ & $3^{rd}$ failure) 44,700 ($4^{th}$ layer failure) 85,000 ($5^{th}$ layer failure) | +45% in Axial Disp. applied as a challenge test to the 4 surviving layers of Test Con. C |

Numerous observations follow from the test data summarized above. Most unexpectedly, a five times (5×) reduction in device layer thickness can yield up to 100× (or more) in fatigue life improvement. This can be seen in comparison of test conditions A and B (the latter of which achieved 95× the average number of cycles (i.e., 17,550) of Test Con. A when testing was terminated prior to device failure). Because Test Con. B was terminated before device failure, it would have likely exceeded this comparative value. Likewise, 4 out of 5 layers of the sample in Test Con. C achieved 98× the cycles of the average of those is Test Con. A when Test Con. C was suspended. Upon instituting the challenge test under Test Con. D, 100× the number of cycles was achieved before any more layers failed in the layered construct. Notably, the eventual failure of additional layers under Test Con. D occurred under dramatically more rigorous testing. Had the original 0.028 mm/cell cycling continued under Test Con. C, there is reason to believe that cycle life of the test article would have further exceeded 100× the fatigue life of the unibody designs (given that tests were terminated before spring member break thus the results reported are so-called "run-out" values). Regardless, the observed improvement of fatigue life seen in Test Cons. B-D evince two orders of magnitude improvement relative to the results of Test Con. A. Stated otherwise, samples designed to differ from each other only in thickness unexpectedly resulted in the thinner samples consistently being able to achieve run-out under the test conditions applied.

Regarding such consistency and the noted possibility of earlier failure of a given single-layer sample (e.g., as in Test Con. C), it is important to note that such a breakage in a multi-layer construct will not significantly degrade overall device function. This is especially true with anchoring heads as described herein continue to retain even the broken layer pieces. The only anticipated consequence is a slight, proportionate drop in available compression force.

Length-Dependent Testing

Further testing was performed of samples configured as above. In this testing, single "unibody" (i.e., 1 mm thick) spring members were tested as well as single 0.2 mm device "layers." The unibody samples were tested at lengths across the tabulated range with 2.5 lbf preload applied; the single layer samples were tested at lengths across the tabulated range with one-sixth of the 2.5 lbf preload applied (given their intended clinical use in a six-layer construct as described herein).

Table 2 presents the estimated fatigue life for a representative median (i.e., $50^{th}$ percentile) device produced via a regression analysis fitting the data generated for a sample size of nine unibody-design specimens. In the table, the bold values across the top indicate the total displacement applied in mm and the bold values along the left side indicate the length of the device subject to such displacement. The values (i.e., number of cycles expected before failure) within the table follow a highly predictable decline in fatigue life in the raw data associated with increased displacement applied relative to device length.

TABLE 2

| | 0.50 | 0.75 | 1.00 | 1.25 | 1.50 | 1.75 | 2.00 | 2.25 | 2.50 | 2.75 | 3.00 |
|---|---|---|---|---|---|---|---|---|---|---|---|
| 40 | 145,000 | 53,825 | 26,700 | 15,525 | 9,980 | 6,868 | 4,960 | 3,730 | 2,885 | 2,290 | 1,850 |
| 45 | 191,889 | 71,700 | 35,578 | 20,722 | 13,300 | 9,136 | 6,610 | 4,960 | 3,846 | 3,047 | 2,470 |
| 50 | 247,000 | 92,300 | 45,900 | 26,700 | 17,200 | 11,800 | 8,530 | 6,410 | 4,960 | 3,940 | 3,190 |
| 55 | 247,000 | 117,000 | 57,973 | 33,709 | 21,682 | 14,900 | 10,745 | 8,085 | 6,260 | 4,960 | 4,022 |
| 60 | 247,000 | 145,000 | 71,700 | 41,650 | 26,700 | 18,367 | 13,300 | 9,980 | 7,733 | 6,135 | 4,960 |
| 65 | 247,000 | 176,077 | 87,146 | 50,592 | 32,454 | 22,362 | 16,123 | 12,146 | 9,388 | 7,451 | 6,032 |

Table 3 was produced in the same manner as Table 2 (i.e., also showing estimates for 50th percentile device based on the test data) with a slightly larger sample size (i.e., with ten device layer samples). Again, the bold values across the top of the table indicate the total displacement applied in mm and the bold values along the left side indicate the length of the device subject to such displacement. Trending like that presented in Table 2 is observed, but with significantly improved fatigue performance of the layers in excess of 1,000,000 (1M) cycles in the multi-layer design under certain tabulated conditions.

TABLE 3

|    | 0.50 | 0.75 | 1.00 | 1.25 | 1.50 | 1.75 | 2.00 | 2.25 | 2.50 | 2.75 | 3.00 |
|----|------|------|------|------|------|------|------|------|------|------|------|
| 40 | >1M  | >1M  | 435,000 | 148,500 | 61,250  | 29,025  | 15,200  | 8,580   | 5,150  | 3,248  | 2,130  |
| 45 | >1M  | >1M  | 773,333 | 261,889 | 108,067 | 51,256  | 26,911  | 15,200  | 9,116  | 5,741  | 3,763  |
| 50 | >1M  | >1M  | >1M     | 435,000 | 180,000 | 85,300  | 44,700  | 25,300  | 15,200 | 9,560  | 6,270  |
| 55 | >1M  | >1M  | >1M     | 694,545 | 286,636 | 136,000 | 71,055  | 40,064  | 24,118 | 15,200 | 9,942  |
| 60 | >1M  | >1M  | >1M     | >1M     | 435,000 | 206,667 | 108,067 | 61,250  | 36,733 | 23,133 | 15,200 |
| 65 | >1M  | >1M  | >1M     | >1M     | 642,615 | 304,615 | 160,000 | 90,262  | 54,162 | 34,131 | 22,362 |

Moreover, the results in both of these tables are generally consistent with those in Table 1. (For comparison between the tables, the approximate displacement per cell in each design (because each cell is approximately 1 mm in length) for any given entry in Tables 2 and 3 can be obtained by dividing a selected device length by the displacement applied.)

Also, it should be noted that the estimates in Tables 2 and 3 represent when a single device layer might be expected to fail. In other words, such performance does not account for the redundancy in the multi-layer designs in which one or more layers may fail while the overall device remains intact.

In addition, it can also be observed from Table 2 and Table 3 that sample fatigue life decreases with the displacement applied per unit length of device. However, various design parameters may be altered in the spring member pattern (i.e., the cut pattern used in producing the subject devices) to ameliorate this effect in shorter implanted devices. Specifically, FIGS. 15A-15C illustrate spring member configuration changes that can be applied in order to increase the cell count per unit length of device (thus reducing axial displacement per cell for a given device length) without introducing other, gross performance-altering changes.

Figure 15A:
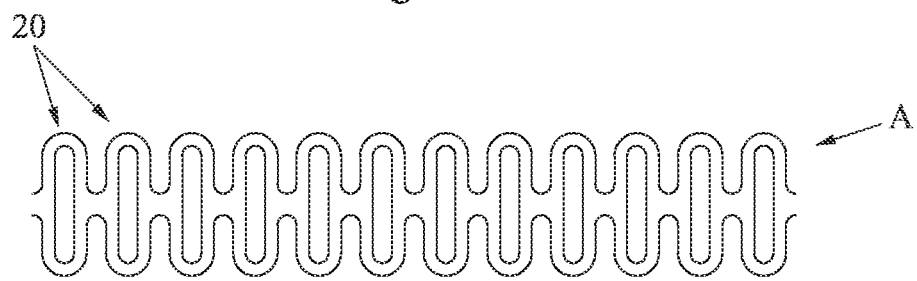
FIGS. 15A-15C illustrate different patterns that may be used for spring members embodiments hereof.
Figure 15B:
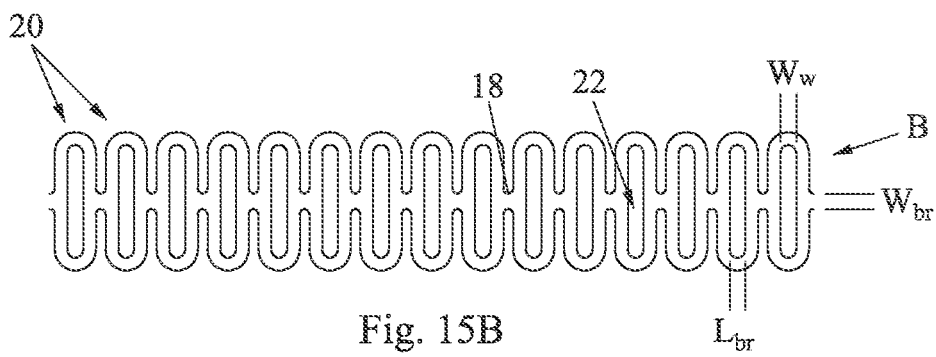
Figure 15C:
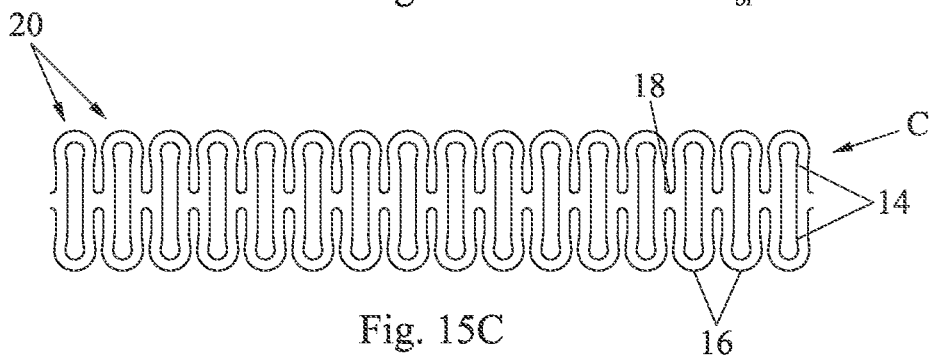

FIG. 15A shows a length of a spring member pattern A. Pattern A corresponds to that shown in the figures and used in the testing referenced above. Pattern B in FIG. 15B differs from pattern A in that it reduces bridge 18 length ($L_{br}$) and aperture or window 22 width ($W_w$). Pattern C in FIG. 15C incorporates the changes of pattern B and also insets bridge 18 position relative to outer connectors 16 (resulting in the curved bar or beam component 14 shapes or "lightbulb" shaped cell ends). Over an equivalent length of 12 cells in pattern A as shown in FIG. 15A, pattern B gains 3 cells to total 15 cells; pattern C gains 4 cells to total 16 over the same relative length. As such, use of pattern C in a spring member will result in a device that experiences the same displacement per cell at 45 mm length as a 60 mm device using pattern A.

Another approach that can be employed to reduce strain per unit cell over a given displacement and active length of a spring member is to decrease the bridge 18 width ($W_{br}$). For a spring member body of same width being compared to another without the change, this increases the relative length of the included bars or beams 14 providing the potential for same axial deflection with reduced peak stress and strain. Alternatively, (or additionally) the overall pattern width may be increased, employing longer beams 14. Yet, doing so may require a larger pilot hole. Thus, it should be clear that the design selected involves a number of competing variables.

Naturally, further changes in spring member pattern may be applied to further improve cyclic fatigue life in shorter device lengths. Aside from the bulk changes described, refinements in shape guided by finite element analysis (FEA) is, of course, possible as well. Regardless, for the subject multi-layer devices, it may be desirable to engage in such pattern design or selection so that any length of implant to be used is subject to axial displacements of less than about 0.025 and about 0.030 mm per cell, or more particularly less than 0.027 or 0.028 mm per cell with the pictured design. Further, these values with vary with different cell configuration as contemplated within the scope of the present disclosure and embodiments hereof.

Digital Hardware

Tension or associated compression measurement force readings in the subject methods may be obtained using commercially available electronic hardware. Strain gauge and piezoelectric sensors used to measure compression and/or tension pulled between portions of a sensor substrate or interface are well known. These may be used herein.

If so, the calculation or processes carried out in connection with the embodiments herein may be implemented or performed with a general or specific purpose processor or processing circuitry, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has a user interface port that communicates with a user interface, and which receives commands entered by a user, has at least one non-transitory memory (e.g., hard drive or other comparable storage, and random access memory) that stores electronic information including a program that operates under control of the processor and with communication via the user interface port, and a video output that produces its output via any kind of video output format, e.g., VGA, DVI, HDMI, USBC, Display Port, or any other form.

A processor may also be implemented as a combination of computing devices, e.g., a combination of a DSP and a microprocessor, multiple microprocessors, one or more microprocessors in conjunction with a DSP core, or any other such configuration. These devices may also be used to select values for devices as described herein The steps of the methods described herein executed by an electronic device may be implemented in hardware, software, firmware, or any combination thereof. If implemented in software, the functions may be encoded as instructions and data in a non-transitory computer-readable medium, for example, a computer memory. When executed by a processor, the encoded instructions may cause an apparatus, for example a flow sensor, to perform a method as described herein. Computer-readable media includes both computer storage media and communication media including any medium that facilitates transfer of a computer program from one place to another. A non-transitory computer-readable medium may include any non-transitory medium suitable for access and decoding by a computer. By way of example, and not limitation, such non-transitory computer-readable media can include RAM, ROM, EEPROM, CD-ROM or other optical disk storage, magnetic disk storage or other magnetic storage devices, or any other medium that can be used to encode desired program code in the form of non-transitory instructions or data structures and that can be accessed by a computer. The memory storage can also be rotating magnetic hard disk drives, optical disk drives, or flash memory based storage drives or other such solid state, magnetic, or optical storage devices. Also, any connection is properly termed a computer-readable medium Operations as described herein can be carried out on or over a website. The website can be operated on a server computer or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

Variations

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible.

In many example embodiments, a device is provided that includes: a spring member including a plurality of layers held together, where each layer of the plurality of layers has an elongate stretchable structure with two lateral outer extents, and where each layer of the plurality of layers includes a plurality of beams arranged in pairs, where a first beam and a second beam of each pair are connected to each other only at the two lateral outer extents such that the first beam opposes the second beam, and where each pair of beams is connected to an adjacent pair of beams by only a medial connector such that gaps are present at the two lateral outer extents between each pair of beams and the adjacent pair of beams. The beams and connectors at the beam outer extents can form a shape selected from rectangle, square, race-track, oval and circle shapes.

In any and all of these embodiments, the spring member layers (and overall stacked construct) advantageously comprise a SE NiTi alloy.

In any and all of these example embodiments, the spring member layers can be individual layers that are held together with at least one weld. Only one weld may be provided, and the weld can be at an end of the spring member.

In any and all of these example embodiments, each layer of the plurality of layers is about 0.01 inches (0.25 mm) thick, e.g., such as between 0.008 inches (0.20 mm) and 0.012 inches (0.30 mm) thick.

In any and all of these example embodiments, the beams have a ratio of width to thickness of between about 2:3 and about 3:2. The ratio can be about 1:1.

In any and all of these example embodiments, the spring member includes at least 2 or 3 or more layers, at least 4 or more layers, at least 5 or more layers, at least 6 or more layers or no more and no less than 3, 4, 5 or 6 layers.

In any and all of these embodiments, the device can further include: an anchoring foot including a first end, a second end and pivot holes therebetween; a longitudinal extension from a distal extent of the beams of each layer, a distal end of each longitudinal extension including an aperture; and a pin received by the anchoring foot pivot holes and the aperture in each longitudinal extension.

In any and all of these embodiments, the device can further include: an anchoring foot including a first end, a second end and pivot holes therebetween; a first spring member piece doubled around a fold so as to form two spring member layers; and a pin received by the anchoring foot pivot holes and at the fold of the spring member piece. The device can further include a second spring member piece folded over the first spring member piece. The device can further include a third spring member piece folded over the second spring member.

In any and all of these embodiments, the device can further include an anchoring head. The anchoring head can have a body and a tooth slidingly received therein, where the tooth is configured to cross the plurality of spring member layers. The body and the tooth can be configured to lock with one another when the tooth is advanced to a locking position within the body. A deflectable latch may be provided for such purposes. In one example, it is in the form of a flexible arm hook that can move side-to-side relative to a base of the anchoring head. In another example, the latch is in the form of a deflectable tang that can move up-and-down relative to a base of the anchoring head. In each case, the end of the latch will lock when received in a pocket or receptacle formed in the anchoring head body.

One or more of these anchors (depending on whether the spring member has a foot attached thereto, as in some embodiments) is included in packaged combination as part of a system or kit. Optionally, the anchor(s) are pre-set or held in a loading device configured to releasably retain an anchor. Such a device advantageously includes a lever arm able to move and deploy the sliding tooth or cross-pin of the anchor prior to its release. Detent features are also advantageously included to assist in use. Specifically, inclusion of such feature(s) advantageously automatically align the anchor and spring member body for deployment of the sliding tooth or another crossing member.

For example, in any and all of these embodiments, the system can include at least one anchor loader for applying an anchor over the spring member, the loader including: a body including a tunnel configured to receive the spring member, a plurality of flexible extensions from the body, each of the flexible extensions including an overhanging tip configured to retain the anchor; and a lever arm connected to the body, the lever arm being able to move toward the body and including a tip configured to push an anchoring tooth of the anchoring head into a final position. The anchor loader can further include at least one detent feature positioned to interact with the spring member to align any of a plurality of windows in the spring member body for anchoring tooth receipt. The at least one detent feature can be positioned to fit between adjacent connectors along a lateral outer extent of the spring member. The at least one detent feature can be integral with the oval base. The system can include two detent features. The spring member, anchor loader and the detent feature can be configured to operate without spring loading the detent feature. In any and all embodiments, the at least one detent feature can include a V-shaped extension.

In any and all of these embodiments, a method of tensioning the subject medical devices (or similarly functional devices) can include setting a position of the proximal anchor with the spring member received through the proximal anchor, pulling the spring member to test the spring member's tension, adjusting the tension of the spring member by pulling additional length of the spring member through the proximal anchor or allowing length of the spring member to retract through the proximal anchor, and locking the proximal anchor. A digital force meter may be used to test the tension of the spring member in the method. Alternatively, the anchor(s) is/are applied to a spring member received within anatomy that is reduced (manually or with a clamp) without such application of tension or preload.

Where a range of values is provided, it is understood that every intervening value, between the upper and lower limit of that range and any other stated or intervening value in the stated range is encompassed within the present subject matter. Also, it is contemplated that any optional feature of the inventive variations described may be set forth and claimed independently, or in combination with any one or more of the features described herein. Moreover, no limitations from the specification are intended to be read into any claims, unless those limitations are expressly included in the claims.

As used herein and in the appended claims, the singular forms "a", "an", and "the" include plural referents unless the context clearly dictates otherwise. In other words, use of the articles allow for "at least one" of the subject items in the description above as well as the claims below. The claims may exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element irrespective of whether a given number of elements are enumerated in the claim, or the addition of a feature could be regarded as transforming the nature of an element set forth in the claims.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

The subject matter described herein and in the accompanying figures is done so with sufficient detail and clarity to permit the inclusion of claims, at any time, in means-plus-function format pursuant to 35 U.S.C. Section 112, Part (f). However, a claim is to be interpreted as invoking this means-plus-function format only if the phrase "means for" is explicitly recited in that claim.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, acts, steps, or elements of the embodiments may be recited in or added to the claims, as well as negative limitations that define the inventive scope of the claims by features, functions, acts, steps, or elements that are not within that scope.

The invention claimed is:

1. A system comprising:
an anchor loader comprising:
an anchor loader body including a tunnel configured to receive a spring member;
a plurality of flexible extensions from the anchor loader body, each of the flexible extensions including an overhanging tip configured to retain an anchor; and
a lever arm connected to the anchor loader body, the lever arm being able to move toward the anchor loader body and including a tip configured to push an anchoring tooth to fix the anchor to the spring member.

2. The system of claim 1, wherein the anchor loader further comprises at least one detent feature positioned to interact with the spring member.

3. The system of claim 2, wherein the at least one detent feature includes a V-shaped extension.

4. The system of claim 3, wherein the spring member further comprises adjacent connectors along a lateral extent of the spring member, and wherein the V-shaped extension is positioned to fit between the adjacent connectors.

5. The system of claim 3, wherein the at least one detent feature comprises a base, and wherein the V-shaped extension is integral with the base.

6. The system of claim 3, wherein the at least one detent feature includes at least two detent features.

7. The system of claim 2, wherein the anchor loader comprises a deflectable beam, and wherein the at least one detent feature of the at least one anchor loader is carried by the deflectable beam.

8. The system of claim 7, wherein the at least one anchor loader comprises a slidable collar, the slidable collar configured for locking the at least one detent feature with the spring member.

9. The system of claim 1, wherein the spring member further comprises adjacent connectors along a lateral extent of the spring member, and the system further comprises at least one spur gear, the at least one spur gear configured and positioned to mesh with the spring member between the adjacent connectors.

10. The system of claim 9, further comprising at least one detent feature to interact with the at least one gear.

11. The system of claim 10, wherein the at least one detent feature comprises a pawl located at the end of a flexible arm.

12. A system comprising:
an anchor head;
a spring member, wherein the spring member has an elongate stretchable structure with a plurality of beams arranged in opposing pairs, and a window is defined by each opposing beam pair;
an anchor loader comprising:
an anchor loader body including a tunnel configured to receive the spring member;
a plurality of flexible extensions from the anchor loader body, each of the flexible extensions including an overhanging tip configured to retain the anchor head; and a lever arm connected to the anchor loader body, the lever arm being able to move toward the anchor loader body and including a tip configured to push an anchoring tooth to fix the anchor head to the spring member.

13. The system of claim 12, wherein the spring member comprises a NiTi alloy that is superelastic at human body temperature.

14. The system of claim 13, wherein the anchor head includes a head base and a channel within the head base, and the anchoring tooth is configured to be pushed into the channel of the head base.

15. The system of claim 14, wherein the anchoring tooth is configured to be advanced within a corresponding window of an opposing beam pair of the opposing beam pairs of the spring member, such that the anchor head is capable of being fixed to the spring member.

* * * * *